United States Patent
Nurmikko et al.

(10) Patent No.: US 12,076,110 B2
(45) Date of Patent: Sep. 3, 2024

(54) LARGE-SCALE WIRELESS BIOSENSOR NETWORKS FOR BIOMEDICAL DIAGNOSTICS

(71) Applicant: Brown University, Providence, RI (US)

(72) Inventors: Arto Nurmikko, Providence, RI (US); Jihun Lee, Providence, RI (US); Ah-Hyoung Lee, Providence, RI (US); Farah Laiwalla, Providence, RI (US)

(73) Assignee: Brown University, Providence, RI (US)

( * ) Notice: Subject to any disclaimer, the term of this patent is extended or adjusted under 35 U.S.C. 154(b) by 11 days.

(21) Appl. No.: 18/048,313

(22) Filed: Oct. 20, 2022

(65) Prior Publication Data

US 2023/0118196 A1    Apr. 20, 2023

Related U.S. Application Data

(60) Provisional application No. 63/257,829, filed on Oct. 20, 2021.

(51) Int. Cl.
*A61B 5/00* (2006.01)
*H04L 1/00* (2006.01)
(Continued)

(52) U.S. Cl.
CPC .......... *A61B 5/0031* (2013.01); *H04L 1/0003* (2013.01); *H04L 27/20* (2013.01);
(Continued)

(58) Field of Classification Search
CPC .. A61B 5/0031; A61B 5/0028; A61B 5/02158
See application file for complete search history.

(56) References Cited

U.S. PATENT DOCUMENTS 5,948,006 A   9/1999 Mann
6,134,474 A   10/2000 Fischell et al.
(Continued)

FOREIGN PATENT DOCUMENTS

CN   101674573 B   5/2012
CN   102480740 A   5/2012
(Continued)

OTHER PUBLICATIONS

"IEEE Recommended Practice for Determining the Peak Spatial-Average Specific Absorption Rate (SAR) in the Human Head from Wireless Communications Devices: Measurement Techniques", IEEE 1528-2013, Sep. 2013, pp. 1-246.
(Continued)

*Primary Examiner* — Wen W Huang
(74) *Attorney, Agent, or Firm* — Adler Pollock & Sheehan P.C.

(57) ABSTRACT

A method includes providing an ensemble of distributed sensors, delivering radio frequency (RF) power to each sensor by inductive near-field coupling by a magnetic field projected by an epidermal transmit (Tx) coil, in each individual sensor, detecting a sparse binary event in its immediate environment, reporting the detected sparse binary event to an external RF receiver hub asynchronously and with low latency, and minimizing error rates due to statistical data packet collisions in asynchronous telemetry by digitally encoding each sensor according to a particular address scheme where each address is one function from an infinite set of mathematically orthogonal functions, enabling a simultaneous detection from up to ten thousand points without interference at a common receiver.

17 Claims, 16 Drawing Sheets

(51) Int. Cl.
*H04L 27/20* (2006.01)
*H04W 74/08* (2024.01)
*H04W 84/18* (2009.01)

(52) U.S. Cl.
CPC ..... *H04W 74/08* (2013.01); *A61B 2560/0219* (2013.01); *H04W 84/18* (2013.01)

(56) References Cited

U.S. PATENT DOCUMENTS

| | | | |
|---|---|---|---|
| 6,409,674 | B1 | 6/2002 | Brockway et al. |
| 6,754,538 | B2 | 6/2004 | Linberg |
| 7,020,505 | B1 | 3/2006 | Phillips et al. |
| 7,212,851 | B2 | 5/2007 | Donoghue et al. |
| 7,647,097 | B2 | 1/2010 | Flaherty et al. |
| 7,751,877 | B2 | 7/2010 | Flaherty et al. |
| 7,881,780 | B2 | 2/2011 | Flaherty |
| 7,901,368 | B2 | 3/2011 | Flaherty et al. |
| 7,989,936 | B2 | 8/2011 | McCain |
| 7,991,461 | B2 | 8/2011 | Flaherty et al. |
| 8,060,194 | B2 | 11/2011 | Flaherty |
| 8,095,209 | B2 | 1/2012 | Flaherty |
| 8,299,912 | B2 | 10/2012 | Otto |
| 8,386,050 | B2 | 2/2013 | Donoghue et al. |
| 8,412,302 | B2 | 4/2013 | Kipke et al. |
| 8,547,248 | B2 | 10/2013 | Zdeblick et al. |
| 8,560,041 | B2 | 10/2013 | Harvey et al. |
| 8,738,139 | B2 | 5/2014 | Lanning et al. |
| 8,812,096 | B2 | 8/2014 | Flaherty et al. |
| 8,818,498 | B2 | 8/2014 | Terada et al. |
| 8,958,868 | B2 | 2/2015 | Ghovanloo et al. |
| 9,028,405 | B2 | 5/2015 | Tran |
| 9,402,544 | B2 | 8/2016 | Yee et al. |
| 9,808,199 | B2 | 11/2017 | Kilsgaard et al. |
| 9,819,074 | B2 | 11/2017 | Muller et al. |
| 9,878,167 | B1 | 1/2018 | He et al. |
| 10,340,408 | B1 | 7/2019 | Katnani et al. |
| 10,433,754 | B2 | 10/2019 | Nurmikko et al. |
| 11,324,444 | B2 | 5/2022 | Jensen et al. |
| 2002/0099412 | A1 | 7/2002 | Fischell et al. |
| 2003/0216666 | A1 | 11/2003 | Ericson et al. |
| 2003/0229382 | A1 | 12/2003 | Sun et al. |
| 2004/0082875 | A1 | 4/2004 | Donoghue et al. |
| 2004/0240527 | A1* | 12/2004 | Giannakis ............... H04J 13/18 375/138 |
| 2005/0137652 | A1 | 6/2005 | Cauller et al. |
| 2005/0143790 | A1 | 6/2005 | Kipke et al. |
| 2005/0267597 | A1 | 12/2005 | Flaherty et al. |
| 2005/0283203 | A1 | 12/2005 | Flaherty et al. |
| 2006/0016753 | A1 | 1/2006 | Sowemimo-Coker et al. |
| 2006/0018990 | A1 | 1/2006 | Bazzo et al. |
| 2006/0049957 | A1 | 3/2006 | Surgenor et al. |
| 2006/0058627 | A1 | 3/2006 | Flaherty et al. |
| 2006/0094974 | A1 | 5/2006 | Cain |
| 2006/0111075 | A1 | 5/2006 | Seol |
| 2006/0149338 | A1 | 7/2006 | Flaherty et al. |
| 2006/0167371 | A1 | 7/2006 | Flaherty et al. |
| 2006/0173259 | A1 | 8/2006 | Flaherty et al. |
| 2006/0195042 | A1 | 8/2006 | Flaherty |
| 2006/0241356 | A1 | 10/2006 | Flaherty |
| 2007/0156126 | A1 | 7/2007 | Flaherty |
| 2007/0169333 | A1 | 7/2007 | Donoghue et al. |
| 2007/0265543 | A1 | 11/2007 | VanSickle et al. |
| 2008/0027347 | A1 | 1/2008 | Harris et al. |
| 2009/0157141 | A1 | 6/2009 | Chiao et al. |
| 2009/0157145 | A1 | 6/2009 | Cauller |
| 2010/0002302 | A1 | 1/2010 | Duparre et al. |
| 2010/0063411 | A1 | 3/2010 | Donoghue et al. |
| 2011/0307079 | A1 | 12/2011 | Oweiss et al. |
| 2012/0203129 | A1 | 8/2012 | Rennaker |
| 2012/0302858 | A1 | 11/2012 | Kidmose et al. |
| 2013/0079849 | A1 | 3/2013 | Perryman et al. |
| 2014/0094674 | A1 | 4/2014 | Nurmikko et al. |
| 2014/0275812 | A1 | 9/2014 | Stivoric et al. |
| 2014/0303452 | A1 | 10/2014 | Ghaffari |
| 2016/0051192 | A1 | 2/2016 | Kang et al. |
| 2016/0103487 | A1 | 4/2016 | Crawford et al. |
| 2016/0143541 | A1 | 5/2016 | He et al. |
| 2017/0014035 | A1 | 1/2017 | Newberry |
| 2017/0031441 | A1 | 2/2017 | Muller et al. |
| 2017/0171071 | A1* | 6/2017 | Turon ............... H04W 4/80 |
| 2017/0231501 | A1 | 8/2017 | Culver et al. |
| 2018/0049636 | A1 | 2/2018 | Miller et al. |
| 2018/0288717 | A1* | 10/2018 | Shellhammer ........ H04L 27/22 |
| 2018/0333587 | A1 | 11/2018 | Howard |
| 2019/0175902 | A1 | 6/2019 | Lee et al. |
| 2019/0261860 | A1 | 8/2019 | Culver et al. |
| 2019/0336001 | A1 | 11/2019 | Zhou et al. |
| 2020/0036487 | A1* | 1/2020 | Hammond ........... H04L 5/0012 |
| 2020/0367749 | A1 | 11/2020 | Nurmikko et al. |
| 2021/0093864 | A1 | 4/2021 | Beauchamp et al. |
| 2021/0100952 | A1 | 4/2021 | Brown |
| 2021/0275070 | A1 | 9/2021 | Schuurkamp et al. |
| 2021/0308468 | A1 | 10/2021 | Shepard et al. |
| 2021/0338127 | A1 | 11/2021 | Cavuto et al. |
| 2021/0398338 | A1 | 12/2021 | Philion et al. |
| 2022/0016774 | A1 | 1/2022 | Amell et al. |

FOREIGN PATENT DOCUMENTS

| | | |
|---|---|---|
| CN | 103169448 A | 6/2013 |
| EP | 3020450 A1 | 5/2016 |
| EP | 3150121 B1 | 10/2018 |
| JP | 2004313419 A | 11/2004 |
| JP | 2005261710 A | 9/2005 |
| JP | 2012249916 A | 12/2012 |
| JP | 2015015548 A | 1/2015 |
| JP | 6125670 B2 | 5/2017 |
| KR | 20090009940 A | 1/2009 |
| WO | 9202176 A1 | 2/1992 |
| WO | 2003061517 A2 | 7/2003 |
| WO | 2008021524 A2 | 2/2008 |
| WO | 2012040401 A3 | 8/2012 |
| WO | 2016110804 A1 | 7/2016 |
| WO | 2016187254 A1 | 11/2016 |
| WO | 2017035530 A1 | 3/2017 |
| WO | 2021016544 A1 | 1/2021 |
| WO | 2022029486 A1 | 2/2022 |

OTHER PUBLICATIONS

"Neurological Devices", Food and Drug Administration, Aug. 4, 2021, 2 pages.

Ahn, et al., "Optimal Design of Wireless Power Transmission Links for Millimeter-Sized Biomedical Implants", IEEE Transactions on Biomedical Circuits and Systems, vol. 10, No. 1, Feb. 2016, pp. 125-137.

Behzad, et al., "The Role of EEG in the Diagnosis and Management of Patients with Sleep Disorders", Journal of Behavioral and Brain Science, vol. 11, Oct. 19, 2021, pp. 257-266.

Benovitski, et al., "Ring and Peg Electrodes for Minimally-Invasive and Long-Term Sub-Scalp EEG Recordings", Epilepsy Research, vol. 135, 2017, pp. 29-37.

Biederman, et al., "A Fully-Integrated, Miniaturized (0.125 mm²) 10.5 µW Wireless Neural Sensor", IEEE Journal of Solid-State Circuits, vol. 48, No. 4, Apr. 2013, pp. 960-970.

Duun-Henriksen, et al., "EEG Signal Quality of a Subcutaneous Recording System Compared to Standard Surface Electrodes", Journal of Sensors, vol. 2015, Article ID 341208, 2015, 10 pages.

England, et al., "Epilepsy Across the Spectrum: Promoting Health and Understanding", Institute of Medicine (US) Committee on the Public Health Dimensions of the Epilepsies. Washington (DC): National Academies Press (US); 2012. The National Academies Collection: Reports funded by National Institutes of Health., 2012, 568 pages.

Fang, et al., "Ultrathin, Transferred Layers of Thermally Grown Silicon Dioxide as Biofluid Barriers for Biointegrated Flexible Electronic Systems", Proceedings of the National Academy of Science, vol. 113, No. 42, Oct. 18, 2016, pp. 11682-11687.

Gao, et al., "A Theory of Multineuronal Dimensionality, Dynamics and Measurement", bioRxiv, Nov. 11, 2017, pp. 1-50.

(56) References Cited

OTHER PUBLICATIONS

Ghamari, et al., "A Survey on Wireless Body Area Networks or eHealthcare Systems in Residential Environments", Sensors, vol. 16, Issue 6, Jun. 7, 2016, 34 pages.
Gliske, et al., "Variability in the Location of High Frequency Oscillations During Prolonged Intracranial EEG Recordings", Nature Communications, vol. 9, No. 2155, 2018, 14 pages.
Granata, et al., "Management of the Patient with Medically Refractory Epilepsy", Expert Review of Neurotherapeutics, vol. 9, No. 12, Dec. 2009, pp. 1791-1802.
Handa, et al., "Open and Free EEG Datasets for Epilepsy Diagnosis", arXiv preprint arXiv:2108.01030v1, Aug. 2, 2021, 6 pages.
Hao, et al., "Wireless Body Sensor Networks for Health-Monitoring Applications", Physiological Measurement, vol. 29, Issue 11, Oct. 9, 2008, pp. R27-R56.
Harrison, et al., "A Low-Power Low-Noise CMOS Amplifier for Neural Recording Applications", IEEE Journal of Solid-State Circuits, vol. 38, No. 6, 2003, pp. 958-965.
Hochberg, et al., "Neuronal Ensemble Control of Prosthetic Devices by a Human with Tetraplegia", Nature, vol. 442, No. 7099, 2006, pp. 164-171.
Houmani, et al., "Diagnosis of Alzheimer's Disease with Electroencephalography in a Differential Framework", PLoS One, vol. 13, No. 3, e0193607, Mar. 20, 2018, pp. 1-19.
Ibrahim, et al., "Safe Inductive Power Transmission to Millimeter-Sized Implantable Microelectronics Devices", 37th Annual International Conference of the IEEE Engineering in Medicine and Biology Society (EMBC), 2015, pp. 817-820.
Jeong, et al., "3-D Hermetic Packaging of Sub-mm Size Implantable Microelectronic Sensors by Atomic Layer Deposition (ALD) for Chronic Use", 2018, 1 page.
Jeong, et al., "Conformal Hermetic Sealing of Wireless Microelectronic Implantable Chiplets by Multilayered Atomic Layer Deposition (ALD)", Advanced Functional Materials, vol. 29, No. 1806440, 2018, pp. 1-10.
Kiani, et al., "Design and Optimization of a 3-Coil Inductive Link for Efficient Wireless Power Transmission", IEEE Transactions on Biomedical Circuits and Systems, vol. 5, No. 6, Dec. 2011, pp. 579-591.
Lecomte, et al., "Silk and Peg as Means to Stiffen a Parylene Probe for Insertion in the Brain: Toward a Double Time-Scale Tool for Local Drug Delivery", Journal of Micromechanics and Microengineering, vol. 25, No. 12, Oct. 19, 2015, pp. 1-12.
Lee, et al., "A Scalable and Low Stress Post-CMOS Processing Technique for Implantable Microsensors", Micromachines, vol. 11, No. 925, 2020, pp. 1-15.
Lee, et al., "An Implantable Wireless Network of Distributed Microscale Sensors for Neural Applications", 2019 9th International IEEE/EMBS Conference on Neural Engineering (NER), 2019, pp. 871-874.
Lee, et al., "Asynchronous Large-Scale Networks for Spatially Distributed Autonomous Wireless RF Event Sensors", , Under review at Nature Portfolio, posted on Oct. 13, 2022, 20 pages.
Lee, et al., "Neural Recording and Stimulation Using Wireless Networks of Microimplants", Nature Electronics, vol. 4, Aug. 2021, pp. 604-614.
Lee, et al., "Wireless Power and Data Link for Ensembles of Sub-mm scale Implantable Sensors near 1GHz", 2018 IEEE Biomedical Circuits and Systems Conference (BioCAS)., 2018, pp. 1-4.
Leung, et al., "A CMOS Distributed Sensor System for High-Density Wireless Neural Implants for Brain-Machine Interfaces", ESSCIRC 2018—IEEE 44th European Solid State Circuits Conference (ESSCIRC)., 2018, pp. 230-233.
Minnikanti, et al., "Lifetime Assessment of Atomic-Layer-Deposited Al2O3—Parylene C Bilayer Coating for Neural Interfaces using Accelerated Age Testing and Electrochemical Characterization", Acta Biomaterialia, vol. 10, Issue 2, Feb. 2014, pp. 960-967.
Moctezuma, Luis Alfredo, "Towards Universal EEG Systems with Minimum Channel Count Based on Machine Learning and Computational Intelligence", Doctoral theses at Norwegian University of Science and Technology, Trondheim, Aug. 2021, 178 pages.
Moradi, et al., "Antenna Design for Implanted Tags in Wireless Brain Machine Interface System", IEEE Antennas and Propagation Society International Symposium, 2013, pp. 2083-2084.
Naik, et al., "Intelligent Communication Module for Wireless Biosensor Networks", Biosensors, Chapter 13, Feb. 2010, pp. 225-240.
Neely, et al., "Recent Advances in Neural Dust: Towards a Neural Interface Platform", Current Opinion in Neurobiology, vol. 50, Jun. 2018, pp. 64-71.
Oto, Maria Meritxell, "The Misdiagnosis of Epilepsy: Appraising Risks and Managing Uncertainty", Seizure, vol. 44, 2017, pp. 143-146.
"International Search Report and Written Opinion dated received for PCT Patent Application No. PCT/US2019/042051, mailed on Nov. 1, 2019", Nov. 1, 2019, 10 pages.
Piyare, et al., "On-Demand LoRa: Asynchronous TDMA for Energy Efficient and Low Latency Communication in IoT", Sensors, vol. 18, No. 3718, Nov. 1, 2018, pp. 1-22.
Ramrakhyani, et al., "Design and Optimization of Resonance-Based Efficient Wireless Power Delivery Systems for Biomedical Implants", IEEE Transactions on Biomedical Engineering, vol. 5, No. 1, Feb. 2011, pp. 48-63.
Rishani, et al., "Wearable, Epidermal and Implantable Sensors for Medical Applications", retrieved from the linkhttps://arxiv.org/abs/1810.00321, Sep. 30, 2018, 48 pages.
Shankar, et al., "Energy-Efficient Protocols for Wireless Communication in Biosensor Networks", IEEE, 12th IEEE International Symposium on Personal, Indoor and Mobile Radio Communications, PIMRC, 2001, pp. D114-D118.
Sigurdsson, et al., "A Method for Large-Scale Implantation of 3D Microdevice Ensembles into Brain and Soft Tissue", Microsystems & Nanoengineering, vol. 6, Article No. 97, 2020, pp. 1-13.
Sigurdsson, et al., "Distributed Delivery of Intracortical Microdevices", 2018, 1 page.
Stirling, et al., "Seizure Forecasting Using a Novel Sub-Scalp Ultra-Long Term EEG Monitoring System", Frontiers in Neurology, vol. 12, Article 713794, Aug. 2021, 11 pages.
Tatum, IV, William O., "Long-Term EEG Monitoring: A Clinical Approach to Electrophysiology", Journal of Clinical Neurophysiology, vol. 18, No. 5, 2001, pp. 442-455.
Tomer, et al., "Advanced Clarity for Rapid and High-Resolution Imaging of Intact Tissues", Nature Protocols, vol. 9 No. 7, Jul. 2014, pp. 1682-1697.
Uchitel, et al., "Wearable, Integrated EEG-fNIRS Technologies: A Review", Sensors, vol. 21, No. 6106, Sep. 12, 2021, 19 pages.
Weisdorf, et al., "Ultra-Long-Term Subcutaneous Home Monitoring of Epilepsy—490 Days of EEG from Nine Patients", Epilepsia, vol. 60, 2019, pp. 2204-2214.
Xie, et al., "Plasma-Assisted Atomic Layer Deposition of Al2O3 and Parylene C Bi-Layer Encapsulation for Chronic Implantable Electronics", Applied Physics Letters, vol. 101, 2012, pp. 093702-1-093702-5.
Yakovlev, et al., "Implantable Biomedical Devices: Wireless Powering and Communication", IEEE Communications Magazine, vol. 50, No. 4, Apr. 2012, pp. 152-159.
Yang, et al., "8.3 A 553F2 2-Transistor Amplifier-Based Physically Unclonable Function (PUF) with 1.67% Native Instability", IEEE International Solid-State Circuits Conference (ISSCC), Feb. 2017, pp. 146-147.
Yeon, et al., "Microfabrication, Assembly, and Hermetic Packaging of Mm-Sized Free-Floating Neural Probes", IEEE Biomedical Circuits and Systems Conference, 2017, pp. 1-4.
Yetisen, et al., "Wearables in Medicine", Advanced Materials, vol. 30, Article 1706910, 2018, 26 pages.
Yin, et al., "A 100-Channel Hermetically Sealed Implantable Device for Chronic Wireless Neurosensing Applications", IEEE Trans. on Biomedical Circuits and Systems, vol. 7, No. 2, Apr. 2013, pp. 115-128.

(56) References Cited

OTHER PUBLICATIONS

Zack, et al., "National and State Estimates of the Numbers of Adults and Children with Active Epilepsy—United States, 2015", MMWR Morbidity and Mortality Weekly Report, vol. 66, No. 31, Aug. 11, 2017, pp. 821-825.
Zhang, et al., "EEG/MEG Based Diagnosis for Psychiatric Disorders", Frontiers in Human Neuroscience, Editorial article, Nov. 2, 2022, 3 pages.
Stratus: Changing the Way the World Looks at EEG Testing, retrieved from the link "https://stratusneuro.com/" on Sep. 9, 2023, 8 pages.
Zhang, et al., "Twenty-Four-Hour Ambulatory Recording of Cerebral Hemodynamics, Systemic Hemodynamics, Electrocardiogramd Actigraphy During People's Daily Activities", Journal of Biomedical Optics, vol. 19, No. 4, 2014, pp. 047003-1-047003-12.
Mehta, et al., "Neuroergonomics: A Review of Applications to Physical and Cognitive Work", Frontiers in Human Neuroscience, vol. 7, Article 889, Dec. 2013, 10 pages.
Moreau, et al., "Near-Infrared Measurements of Brain Oxygenation in Stroke", Neurophotonics, vol. 3, No. 3, 2016, pp. 031403-1-031403-8.
Murata, et al., "Changes in Cerebral Blood Oxygenation Induced by Deep Brain Stimulation: Study by Near-Infrared Spectroscopy (NIRS)", Keio Journal of Medicine, vol. 49, Suppl 1, 2000, pp. A61-A63.
Nagaoka, et al., "Development of a New Rehabilitation System Based on a Brain-Computer Interface Using Near-Infrared Spectroscopy", Advances in Experimental Medicine and Biology, vol. 662, 2010, pp. 497-503.
Nemoto, et al., "Microvascular Shunts in The Pathogenesis of High Intracranial Pressure", Acta Neurochirurgica Supplement, vol. 118, 2013, pp. 205-209.
Nolte, et al., "Holographic tissue dynamics spectroscopy", Journal of Biomedical Optics, vol. 16, Issue 8, 2011, pp. 087004-1-087004-13.
Nurmikko, et al., "Wireless Neurotechnology for Neural Prostheses in Neurobionics: The Biomedical Engineering of Neural Prostheses", Neurobionics: The Biomedical Engineering of Neural Prostheses, First Edition, 2016, pp. 123-161.
Okada, et al., "Theoretical and Experimental Investigation of Near-Infrared Light Propagation in a Model of the Adult Head", Applied Optics, vol. 36, No. 1, Jan. 1, 1997, pp. 21-31.
Patterson III, et al., "CMOS ICs for Brain Implantable Neural Recording Microsystems", Applications of CMOS circuits in Biology, R. Westervelt and H. Lee Eds., 2007, pp. 259-291.
International Search Report and Written Opinion Received for PCT Patent Application No. PCT/US2012/029664, dated Jul. 18, 2012, 10 pages.
Peng, et al., "fNIRS-EEG Study of Focal Interictal Epileptiform Discharges", Epilepsy Research, vol. 108, 2014, pp. 491-505.
Petrantonakis, et al., "Single-Trial NIRS Data Classification for Brain-Computer Interfaces Using Graph Signal Processing", IEEE Transactions on Neural Systems and Rehabilitation Engineering : A Publication of the IEEE Engineering in Medicine and Biology Society, vol. 26, 2018, 10 pages.
Rizzolatti, et al., "Motor and Cognitive Functions of the Central Premotor Cortex", Current Opinion in Neurobiology, vol. 12, 2002, pp. 149-154.
Saha, et al., "Compact fast optode-based probe for single-photon counting applications", IEEE Photonics Technology Letters, vol. 30, Issue 17, Sep. 2018, pp. 1515-1518.
Saha, Sreenil, "Miniaturized Optical Probes for Near Infrared Spectroscopy", Ecole Polytechnique, Montreal (Canada), 2018, 167 pages.
Saha, et al., "Miniaturized Probe for Time-Domain Near-Infrared Spectroscopy", IEEE Biomedical Circuits and Systems Conference (BioCAS)., 2018, 4 pages.
Sen, et al., "Clinical Application of Near-Infrared Spectroscopy in Patients with Traumatic Brain Injury: a Review of the Progress of the Field", Neurophotonics, vol. 3, 2016, pp. 031409-1-031409-5.
Shin, et al., "Performance Enhancement of a Brain-Computer Interface Using High-Density Multi-Distance NIRS", Scientific Reports, vol. 7, 16545, 2017, 10 pages.
Song, et al., "A Brain Implantable Microsystem With Hybrid RF/IR Telemetry for Advanced Neuroengineering Applications", Proceedings of 29th Annual International Conference of the IEEE EMBS, 2007, pp. 445-448.
Song, et al., "Development of a Chipscale Integrated Microelectrode/ Microelectronic Device for Brain Implantable Neuroengineering Applications", IEEE Transactions on Neural Systems and Rehabilitation Engineering vol. 13, No. 2, 2005, pp. 220-226.
Strangman, et al., "A Quantitative Comparison of Simultaneous BOLD fMRI and NIRS Recordings During Functional Brain Activation", Neuroimage, vol. 17, 2002, pp. 719-731.
Strangman, et al., "Depth Sensitivity and Source-Detector Separations for Near Infrared Spectroscopy Based on the Colin27 Brain Template", PLoS One, vol. 8, Issue 8, e66319, Aug. 2013, 13 pages.
Strangman, et al., "Near-Infrared Spectroscopy and Imaging for Investigating Stroke Rehabilitation: Test-Retest Reliability and Review of The Literature", Archives of Physical Medicine and Rehabilitation, vol. 87, Suppl 2, Dec. 2006, pp. S12-S19.
Strangman, et al., "Non-Invasive Neuroimaging Using Near-Infrared Light", Biological Psychiatry, vol. 52, 2002, pp. 679-693.
Strangman, et al., "Scalp and Skull Influence on Near Infrared Photon Propagation in the Colin27 Brain Template", Neuroimage, vol. 85, 2014, pp. 136-149.
Strangman, et al., "Wearable Brain Imaging with Multimodal Physiological Monitoring", Applied Physiology, vol. 124, 2018, pp. 564-572.
Torricelli, et al., "In Vivo Optical Characterization of Human Tissues from 610 to 1010 nm by Time-Resolved Reflectance Spectroscopy", Physics in Medicine and Biology, vol. 46, 2001, pp. 2227-2237.
Tsow, Francis, et al., "Wearable Functional Near-Infrared (FNIR) Technology and its Applications in Naturalistic Conditions", American Journal of Biomedical Science & Research, vol. 5, No. 1, Sep. 3, 2019, pp. 33-38.
Ulku, Arin C, et al., "A 512×512 S SPAD Image Sensor with Integrated Gating for Widefield Flim", IEEE Journal of Selected Topics in Quantum Electronics, 2018, 12 pages.
Urban, et al., "Chronic Assessment of Cerebral Hemodynamics During Rat Forepaw Electrical Stimulation Using Functional Ultrasound Imaging", Neuroimage, vol. 101, Nov. 1, 2014, pp. 138-149.
Villringer, et al., "Non-Invasive Optical Spectroscopy and Imaging of Human Brain Function", Trends Neuroscience, vol. 20, No. 10, 1997, pp. 435-442.
Watanabe, et al., "Noninvasive Cerebral Blood Volume Measurement During Seizures Using Multichannel Near Infrared Spectroscopic Topography", Journal of Biomedical Optics, vol. 5, No. 3, Jul. 2000, pp. 287-290.
White, et al., "Quantitative Evaluation of High-Density Diffuse Optical Tomography: In Vivo Resolution and Mapping Performance", Journal of Biomedical Optics, vol. 15, No. 2, 2010, pp. 026006-1-026006-14.
Wu, et al., "Quantitative Evaluation of Atlas-Based High-Density Diffuse Optical Tomography for Imaging of the Human Visual Cortex", Biomedical Optics Express, vol. 5, 2014, pp. 3882-3900.
Wyser, Dominik, et al., "Wearable and Modular Functional Near-Infrared Spectroscopy Instrument with Multidistance Measurements at four Wavelengths", Neurophotonics, vol. 4, No. 4, 2017, pp. 041413-1-041413-13.
Yin, et al., "Wireless Neurosensing Platform for Unconstrained Brain Research", Neuron, vol. 45, Issue 5, 2014, 13 pages.
Zhang, et al., "Adaptive Filtering to Reduce Global Interference In Non-Invasive NIRS Measures of Brain Activation: How Well and When Does It Work?", NeuroImage, vol. 45, 2009, pp. 788-794.
Zhang, et al., "Coregistered Tomographic X-Ray and Optical Breast Imaging: Initial Results", Journal of Biomed Optics, vol. 10, No. 2, 2005, pp. 024033-1-024033-9.
Zhang, et al., "Development of Motion Resistant Instrumentation for Ambulatory Near-Infrared Spectroscopy", Journal of Biomedical Optics, vol. 16, No. 8, Aug. 2011, pp. 087008-1-087008-12.

(56) References Cited

OTHER PUBLICATIONS

Zhang, et al., "Experimental Comparison of Using Continuous-Wave and Frequency-Domain Diffuse Optical Imaging Systems to Detect Heterogeneities", Optical Tomography and Spectroscopy of Tissue IV, Proceedings of SPIE, vol. 4250, 2001, pp. 219-238.
Zhang, et al., "Study of Near Infrared Technology for Intracranial Hematoma Detection", Journal of Biomedical Optics, vol. 5, No. 2, 2000, pp. 206-213.
"International Search Report and Written Opinion received for PCT Patent Application No. PCT/US2023/066014, mailed on Sep. 27, 2023", 13 pages.
"International Search Report and Written Opinion received for PCT Patent Application No. PCT/US2023/078505, mailed on Apr. 10, 2024", 11 pages.
Office Action Received for CN Patent Application No. 201280024098.3, dated Mar. 18, 2015, 9 pages.
Altman, et al., "Measurement in Medicine: The Analysis of Method Comparison Studies", Journal of Royal Statistical Soc Series, vol. 32, 1983, pp. 307-317.
Bevilacqua, Frederic, et al., "In Vivo Local Determination of Tissue Optical Properties: Applications to Human Brain", Applied Optics, vol. 38, No. 22, Aug. 1, 1999, pp. 4939-4950.
Bland, et al., "Agreement Between Methods of Measurement with Multiple Observations Per Individual", Journal of Biopharmaceutical Statistics, vol. 17, 2007, pp. 571-582.
Bland, et al., "Measuring Agreement in Method Comparison Studies", Statistical Methods in Medical Research, vol. 8, 1999, pp. 135-160.
Blodgett, et al., "Brain Imaging for Neural Tissue Health Assessment.", Micro-and Nanotechnology Sensors, Systems, and Applications X, Proceedings of SPIE, vol. 10639, 2018, pp. 106391G-1-106391G-9.
Bluestone, et al., "Three-Dimensional Optical Tomography of Hemodynamics in the Human Head", Optics Express, vol. 9, No. 6, 2001, pp. 272-286.
Borton, et al., "An Implantable Wireless Neural Interface for Recording Cortical Circuit Dynamics in Moving Primates", Journal of Neural Engineering, vol. 10, No. 026010, 2013, 16 pages.
Chen, Songtao, et al., "A Photonic Crystal Laser from Solution Based Organo-Lead Iodide Perovskite Thin Films", ACS Nano, American Chemical Society, vol. 10, No. 4, 2016, pp. 3959-3967.
Chen, et al., "Excitonic Gain and Laser Emission from Mixed-Cation Halide Perovskite Thin Films", Optica, vol. 5, No. 9, Sep. 2018, pp. 1141-1149.
Chestek, et al., "HermesC: Low-Power Wireless Neural Recording System for Freely Moving Primates", IEEE Transactions on Neural Systems and Rehabilitation Engineering, vol. 17, No. 4, Aug. 1, 2009, pp. 330-338.
Choi, Jeehyun, et al., "Noninvasive Determination of the Optical Properties of Adult Brain: Near-Infrared Spectroscopy Approach", Journal of Biomedical Optics, vol. 9, No. 1, 2004, pp. 221-229.
Choquette, K.D., "Vertical Cavity Surface Emitting Lasers (VCSELs)", Chapter 8 in Semiconductor Lasers: Fundamentals and Applications, (Woodhead Publishing Series in Biomaterials), 2013, pp. 316-340.
Chu, Baocheng, et al., "Cerebral Blood Flow on Xenon CT: Correlation with the Blood Flow Detected at the Common Carotid Artery on Ultrasonography", The Keio Journal of Medicine, Suppl 1, 2000, pp. A64-A67.
Churchland, PS, et al., "A Critique of Pure Vision", In: Computational Neuroscience Series: Large Scale Neuronal Theories of the Brain, MIT Press, 1994, pp. 22-60.
Cohen, Jacob, "A Power Primer", Psychological Bulletin, vol. 112, No. 1, 1992, pp. 155-159.
Culver, et al., "Volumetric Diffuse Optical Tomography of Brain Activity", Optics Letters, vol. 28, No. 21, Nov. 1, 2003, pp. 2061-2063.
Cunningham, John E, et al., "Scaling Vertical Cavity Surface Emitting Laser Reliability for Petascale Systems", Applied Optics, vol. 45, No. 25, Sep. 1, 2006, pp. 6342-6348.
Dalla Mora, Alberto, et al., "Towards Next-Generation Time-Domain Diffuse Optics For Extreme Depth Penetration And Sensitivity", Biomedical Optics Express, vol. 6, Issue 5, 2015, pp. 1749-1760.
Duran, et al., "Compressive Imaging in Scattering Media", Optics Express, vol. 23, No. 11, May 22, 2015, pp. 14424-14433.
Ebeling, et al., "Vertical-Cavity Surface-Emitting Laser Technology Applications with Focus on Sensors and Three-Dimensional Imaging", Japanese Journal of Applied Physics, vol. 57, 2018, pp. 08PA02-1-08PA02-11.
Eggebrecht, et al., "A Quantitative Spatial Comparison of High-Density Diffuse Optical Tomography and fMRI Cortical Mapping", Neuroimaging, vol. 61, 2012, pp. 1120-1128.
Eggebrecht, et al., "Mapping Distributed Brain Function and Networks with Diffuse Optical Tomography", Nature Photonics, vol. 8, May 18, 2014, 7 pages.
Extended European Search Report Received for EP Patent Application No. EP12758264.1, dated Sep. 1, 2014, 9 pages.
EPC, "Time-of-Flight Chips", Espros Photonics Corporation, Retrieved on Feb. 28, 2024, Available at <https://www.espros.com/sensor-products/chips/time-of-flight-chips/>, 5 pages.
Fang, et al., "Monte Carlo Simulation of Photon Migration in 3D Turbid Media Accelerated by Graphics Processing Units", Optics Express, vol. 17, No. 22, 2009, pp. 20178-20190.
Ferrari, et al., "A Brief Review on the History of Human Functional Near-Infrared Spectroscopy (fNIRS) Development and Fields of Application", Neuroimage, vol. 63, 2012, pp. 921-935.
Firbank, et al., "Measurement of the Optical Properties of the Skull in the Wavelength Range 650-950 nm.", PhysMedBio, vol. 38, 1993, pp. 503-510.
Franceschini, et al., "Diffuse Optical Imaging of the Whole Head", Journal of Biomedical Optics, vol. 11, No. 5, 2006, pp. 054007-1-054007-10.
Geib, et al., "Fabrication and Performance of 2-Dimensional Matrix Addressable Arrays of Integrated Vertical Cavity Lasers and Resonant Cavity Photodetectors", IEEE Journal of Selected Topics in Quantum Electronics, vol. 8, No. 4, 2002, pp. 943-947.
Gramann, et al., "Cognition in Action: Imaging Brain/Body Dynamics in Mobile Humans", Reviews in the Neurosciences, vol. 22, No. 6, 2011, pp. 593-608.
Grassi, et al., "Near-Infrared Spectroscopy and Skeletal Muscle Oxidative Function In Vivo in Health and Disease: A Review from an Exercise Physiology Perspective", Journal of Biomedical Optics, vol. 21, No. 9, Sep. 2016, pp. 091313-1-091313-20.
Gwin, et al., "Electrocortical Activity is Coupled to gait Cycle Phase During Treadmill Walking", Neuroimage, vol. 54, 2011, pp. 1289-1296.
Harrison, et al., "A Low-Power Integrated Circuit for a Wireless 100-Electrode Neural Recording System", IEEE Journal of Solid-State Circuits, vol. 42, No. 1, 2007, pp. 123-133.
Harrison, et al., "Wireless Neural Recording With Single Low-Power Integrated Circuit", IEEE Transactions on Neural Systems and Rehabilitation Engineering, vol. 17, No. 4, Aug. 1, 2009, pp. 322-329.
Heelan, et al., "A Mobile Embedded Platform for High Performance Neural Signal Computation and Communication", Biomedical Circuits and Systems Conference (BioCAS), 2015, 4 pages.
Heelan, et al., "FPGA implementation of deep-learning recurrent neural networks with sub-millisecond real-time latency for BCI-decoding of large-scale neural sensors (104 nodes)", 40th Annual International Conference of the IEEE on Engineering in Medicine and Biology, 2018, pp. 1070-1073.
Hu, et al., "Ambulatory Diffuse Optical Tomography and Multimodality Physiological Monitoring System for Muscle And Exercise Applications", Journal of Biomedical Optics, vol. 21, No. 9, 2016, pp. 091314-1-091314-14.
Hueber, et al., "Non-Invasive and Quantitative Near-Infrared Haemoglobin Spectrometry in the Piglet Brain During Hypoxic Stress, Using a Frequency-Domain Multidistance Instrument", Physics in Medicine and Biology, vol. 46, 2001, pp. 41-62.
Huppert, et al., "A Temporal Comparison of BOLD, ASL, and NIRS Hemodynamic Responses to Motor Stimuli in Adult Humans.", Neuroimage, vol. 29, 2006, pp. 368-382.

(56) References Cited

OTHER PUBLICATIONS

Izzetoglu, Kurtulus, et al., "Functional Near-Infrared Neuroimaging", In: Proceedings of the Annual International Conference of the IEEE Engineering in Medicine and Biology Society, vol. 1-7, 2004, pp. 5333-5336.

Kasten, et al., "Fabrication and Characterization of Individual Addressable Vertical Cavity Surface Emitting Laser Arrays and Integrated VCSEL/PiN Detector Arrays", Proc. SPIE, vol. 6484, 2007, pp. 64840C-1-64840C-6.

Leon-Carrion, et al., "The Infrascanner, a Handheld Device for Screening in Situ for the Presence of Brain Haematomas", Brain Injury, vol. 24, No. 10, Sep. 2010, pp. 1193-1201.

Li, et al., "Reconstructing Chromosphere Concentration Images Directly by Continuous-Wave Diffuse Optical Tomography", Optics Letters, vol. 29, No. 3, Feb. 1, 2004, pp. 256-258.

Liutkus, et al., "Imaging With Nature: Compressive Imaging Using a Multiply Scattering Medium", Scientific Reports, vol. 4, 5552, 2014, 7 pages.

Makeig, et al., "Linking Brain, Mind and Behavior", International Journal of Psychophysiology, vol. 73, 2009, pp. 95-100.

Malcolm, et al., "The Aging Brain Shows Less Flexible Reallocation of Cognitive Resources During Dual-Task Walking: A Mobile Brain/Body Imaging (MoBI) Study", Neuroimage, vol. 117, 2015, 13 pages.

Mateo, et al., "Entrainment of Arteriole Vasomotor Fluctuations by Neural Activity Is a Basis of Blood-Oxygenation-Level-Dependent "Resting-State" Connectivity", Neuron, vol. 96, No. 4, Nov. 15, 2017, 17 pages.

\* cited by examiner

LARGE-SCALE WIRELESS BIOSENSOR NETWORKS FOR BIOMEDICAL DIAGNOSTICS

CROSS REFERENCE TO RELATED APPLICATIONS

This application claims benefit from U.S. Provisional Patent Application Ser. No. 63/257,829, filed Oct. 20, 2021, which is incorporated by reference in its entirety.

BACKGROUND OF THE INVENTION

The present invention relates generally to sensor networks, and more particularly to large-scale wireless biosensor networks for biomedical diagnostics.

In general, multipoint sensors are needed for many biomedical diagnostic applications where each sensor records local activity from a complex physiological circuit. In particular, wearable and implantable spatially distributed sensors can play a key role in collecting the information needed to reconstruct the physiological state dynamics of such circuits as in the brain, in the heart, in muscles, and other internal organs.

Demonstrations of various sensors, aimed at either the central or the peripheral nervous system, have been limited to single or a small handful of devices as the technical challenge to build a large-scale multipoint sensor require new innovations.

BRIEF SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention features a method including providing an ensemble of distributed sensors, delivering radio frequency (RF) power to each sensor by inductive near-field coupling by a magnetic field projected by an epidermal transmit (Tx) coil, in each individual sensor, detecting a sparse binary event in its immediate environment, reporting the detected sparse binary event to an external RF receiver hub asynchronously and with low latency, and minimizing error rates due to statistical data packet collisions in asynchronous telemetry by digitally encoding each sensor according to a particular address scheme where each address is one function from an infinite set of mathematically orthogonal functions, enabling a simultaneous detection from up to ten thousand points without interference at a common receiver.

In another aspect, the invention features a system including independent sensors, each of the independent sensors digitally encoded on-chip according to a particular address scheme, an epidermal transmit (Tx) coil, the Tx coil delivering radio frequency (RF) power to each of the plurality of independent sensors, the Tx coil capturing asynchronous data emitted from each of the plurality of sensors by radio frequency (RF) backscattering, and an external radio frequency (RF) receiver hub.

In still another aspect, the invention features a method including providing a communication protocol between an external RF transceiver hub and an ensemble of distributed individual sensors, in each individual sensor, detecting a sparse binary event in its immediate environment, reporting the detected sparse binary event to an external RF hub asynchronously and with low latency, and minimizing error rates due to statistical data packet collisions in asynchronous telemetry by digitally encoding each sensor according to a particular address scheme where each address is one function from an infinite set of mathematically random or orthogonal functions, enabling the simultaneous detection from up to ten thousand points without interference at the common receiver.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE SEVERAL VIEWS OF THE DRAWING

These and other features, aspects, and advantages of the present invention will become better understood with reference to the following description, appended claims, and accompanying drawings where:

DETAILED DESCRIPTION OF THE INVENTION

Figure 1:
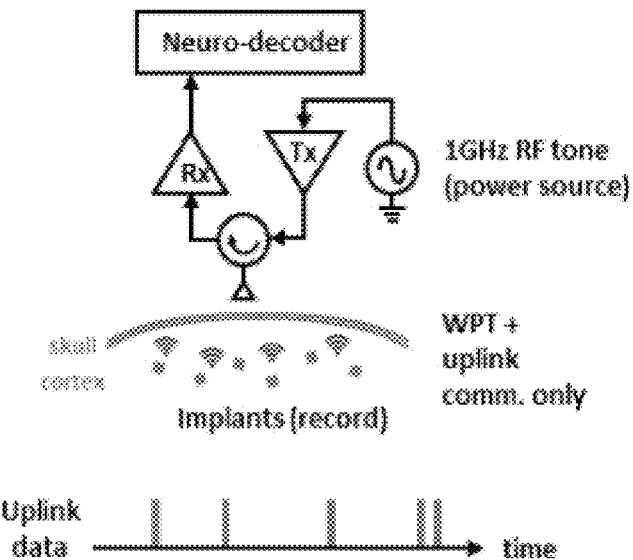
FIG. 1 is a diagram.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

The present invention is a system and method to measure internal states of the body by a large wireless network of spatially distributed unobtrusive sensors. The individual sensors are spatially distributed silicon chiplets which are either implanted in the body or applied to the surface of the skin. Physiological signals are measured from each autonomous sensor locally and transmitted wirelessly to a common radio-frequency (RF) antenna-receiver. To enable a large number of sensors to stream their data in real time, the present invention includes specific telemetry protocols to achieve low error rates and low latency.

In FIG. 1, an exemplary individual microprobe sensor is shown, here specific to a brain implant. Each such device is an autonomous unit that either records neural activity from nearby neurons or stimulates local circuits by current injection. We have developed scalable and agile networking solutions for large ensembles of implantable neurograins. An external ratio frequency (RF) hub coordinates bidirectional transmission of digital data, further linking neurograin populations to downstream computational platforms for decoding and encoding the data.

In the embodiment illustrated in FIG. 1, each sensor in an ensemble of thousands of such distributed devices, detects a biosignal of interest at one specific microscale location. Whenever any sensor detects a sparse binary event in its immediate environment, such as, for example, a neural cell action potential, it reports the event to an external RF receiver hub asynchronously and with low latency.

Figure 2:
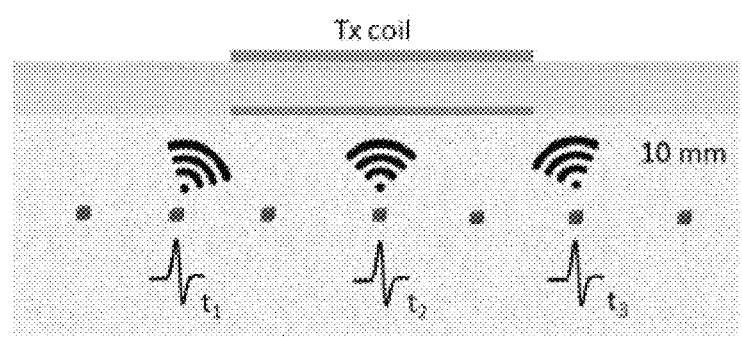
FIG. 2 is a diagram.

This "detect and immediate transmit" principle is shown schematically in FIG. 2, enabling the entire network to achieve efficient multipoint digital transmission with minimal system simplicity and power. Error rates due to statistical data packet collisions in the asynchronous telemetry are minimized by digitally encoding each sensor according to a particular address scheme. The telemetry subcircuits of the sensor ASICs are designed for binary phase shift key (BPSK) modulation. The approach below is termed an asynchronous sensor network, here designed specifically for biomedical implants/wearables.

Suppose that we have an ensemble of autonomous microprobes with each equipped with a unique electronic address. The analog circuit portion on the chip is configured to accept neural signals from the pair of microelectrodes (i.e., gradient in the neural potential near a neuron), filter lower frequency components and using a comparator subcircuit to set a threshold, record spikes only from the continuous background. The on-board digital engine is designed to automatically transmit a spiking event within a millisecond window as an "uplink" data packet to the external receiver. This scheme does not require any instructions from the external unit (i.e., no "downlink" commands), only RF power delivered to each neurograin by inductive near-field coupling via the magnetic field projected by the epidermal Tx coil (here near 1 GHz).

Figure 3:
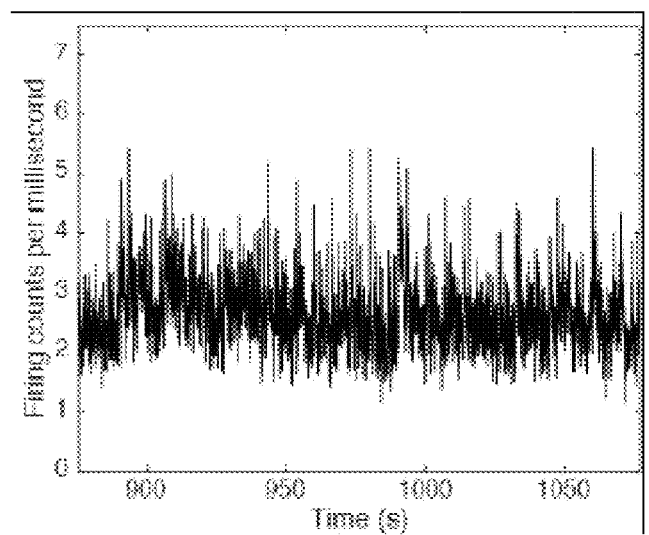
FIG. 3 is a graph.

To illustrate the anticipated data streams arriving at the external receiver for an ensemble of imagined implanted neurograins, FIG. 3 illustrates a superposition of raw spiking data from simultaneous recording by 96 microelectrodes from a 'Utah' array, implanted into the auditory cortex of a macaque monkey. Using this type of data, we have synthesized a hypothetical case of an aggregate of 960 simultaneous channels (each neuron with a Poisson spike distribution and average firing rate of 20 spikes per second). This gives an estimate of roughly five spikes occurring every one millisecond, therefore framing the requirement for the data date in the telemetry for a network of neurograins. Given the sparsity of spiking, even in a highly active cortical circuit, requires only an approximate bandwidth of 10 Mbps for an ensemble of many thousands of neurograins.

The challenge for a large ensemble of implanted microprobes, i.e., reporting detected events (spikes) from up to a thousand distinct microscale locations through a single common transmission channel, is to identify and separate the individual contributions in the received data for subsequent analysis of the neural (or other phycological cellular level) population dynamics. On one hand, the (~30 MHz) clocks on board the neurograins are independent and free running thereby lacking synchrony even across an ensemble of nominally identical transmitters. On the other hand, the concept of an asynchronous detect and transmit paradigm for sparse events is attractive in its simplicity while the moderate bandwidth requirements offer the opportunity to operate a large-scale network. Here we explicitly assume that each intracortical microprobe will report detected spike events by transmitting a spread bit sequence (bit '1') and remains silent otherwise (bit '0'). Given the intrinsic sparsity of spike activity even in a highly active cortical circuit (~20 spikes/s per neuron on average; each chip operates at a low duty cycle and switches on its uplink only when the detection circuits recognizes an above threshold event. We have explored various digital modulation schemes on test chips (e.g., ASK, BPSK, ASK-PWM) to demonstrate up to 10 Mbps speeds with various chip architectures, a data rate sufficient to accommodate to thousands neurograins.

Figure 4:
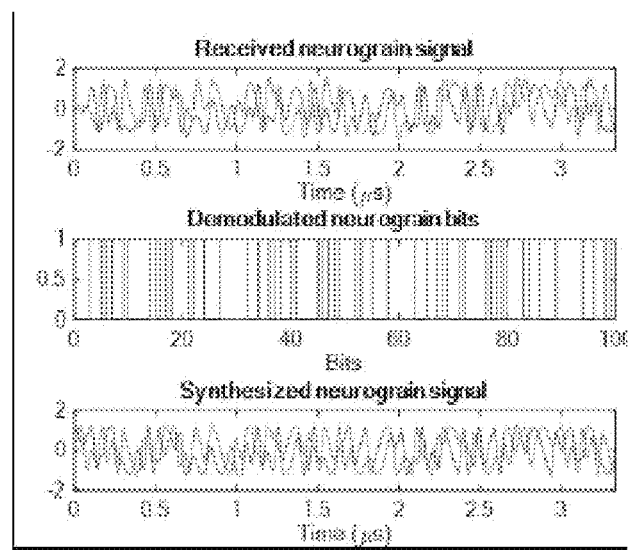
FIG. 4 is a graph.

FIG. 4 shows an example of a computer simulation where a BPSK modulated RF backscattered sample neural data string is detected by IQ demodulation, and then reconstructed at high fidelity by the decoding algorithm.

In an asynchronous digital transmission scheme, a main source of errors occurs due to data packet collisions. Statistically, any two neurograins can detect and uplink their data nearly simultaneously, thus there is the probability that data packets overlap, i.e., a partial packet collision event occurs. This is a fundamental problem for a large ensemble of transmitters which use the same transmission channel.

We employ a particular packet encoding strategy to improve the bit transmission fidelity at the RF backend to minimize the error-rates due to packet collisions on one hand while maximizing the number of neurograins allowed in a network on the other hand. We have demonstrated the utility of the on-chip PUF addressing method for both the recording and stimulating versions of the epicortical (larger footprint) ASICs. To enable scaling the multipoint system to large ensembles of microprobes we add another layer in the digital identification. In particular we use an additional unique spreading code, embedded on each chip, namely the Gold code in Code-division multiple access (CDMA)-type digital communication. Mathematically, Gold codes have bounded small cross-correlations within a finite set of codes such as used in mobile communications when multiple devices are broadcasting in the same frequency range. In hardware on the chip scale, a Gold code can be implemented in a linear shift registers (LSFR) architecture, in very small footprint circuits in the 65 nm RF CMOS process while requiring minimal digital processing on the chip itself.

Figure 5:
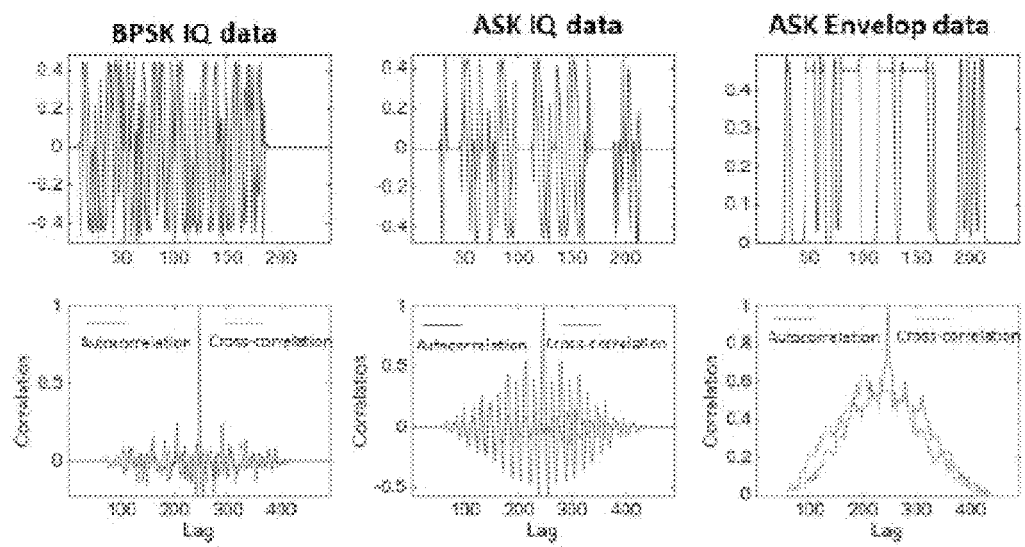
FIG. 5 are graphs.

Simulations have been carried out to test and compare the encoding of PUF and Gold codes by different combinatorial modulation approaches in the recovery of binary data such as spikes for large ensembles of neurograins. FIG. 5 compares the recovery of RF backscattered BPSK, ASK, and ASK envelope data, respectively, and the associated auto- and cross-correlations for Gold code of order L=6. In this example, the autocorrelation for the BPSK IQ data appears to offer a better option.

Figure 6:
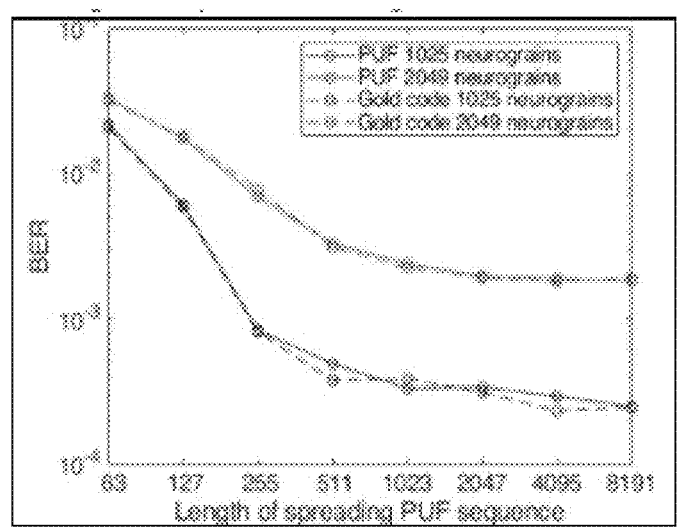
FIG. 6 is a graph.

We have compared the performance of PUF-codes and Gold-codes in terms of statistical transmission/demodulation bit error rates (BER). FIG. 6 shows a sample test case assuming 1025 and 2049 neurograins in the network, respectively. The simulation is shown for the BER as a function of the code length of the PUF component, suggesting that a spreading sequence of at least 1023 is needed (a relatively long code but still with acceptable system latency on a msec timescale. We note that the BER (fidelity of digital transmission) differs from the recently introduced 'spike error rate' (SER), the latter describing statistical errors due to sparse sampling by spike-detection circuit of neuronal firing.

Figure 7:
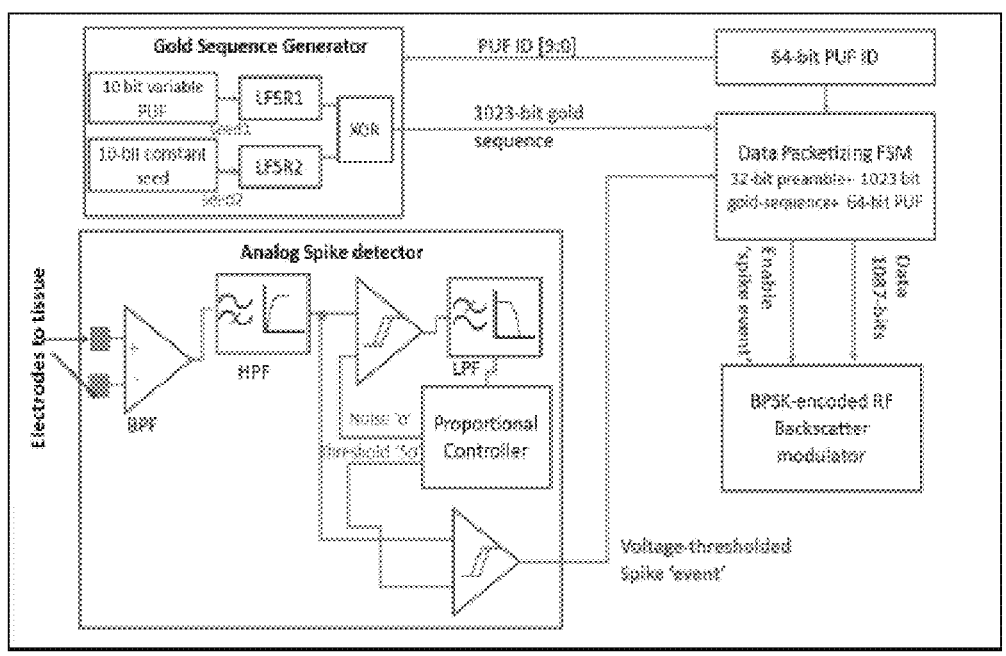
FIG. 7 is a block diagram.

For in-silico implementation of the theoretical network models, we show one exemplary chip design for the PUF-Gold spreading code, shown at a block diagram level in FIG. 7. In addition to a simple threshold-detecting analog front end, the circuit embeds the coding scheme for a BPSK backscattering modulator, seeding a 1023-bit gold code with a PUF seed.

In summary, the present invention is a RF-based communication approach for a network of microchip sensors that is scalable to many thousands of nodes. The method makes efficient use of the spectrum without the need for global synchronization through a novel code modulation by a CDMA-type approach. The approach is inspired by principles of information processing in the brain as understood today, where neuronal packets of information are sparse, binary "spike firing" events. Here each sensor is a remotely powered, millimeter-scale, microwatt-power integrated circuit chip. One goal is to lay the engineering foundation for an implantable sensor network to enable predictive modeling of state dynamics of a functional area of the brain cortex. More broadly, the target environment of interest may be another physiological circuit in the human body, assets in a warehouse with a rapidly changing inventory, interaction-driven vehicular or human traffic pattern, and in general a heterogeneous interactive environment in forecasting future trajectory is of importance. Our particular motivation is to develop wireless brain sensors for future application to brain-machine interfaces (BMI), an application where recording from a handful of implanted microelectrodes has demonstrated the operation of external assistive devices by direct cortical commands.

Figure 8:
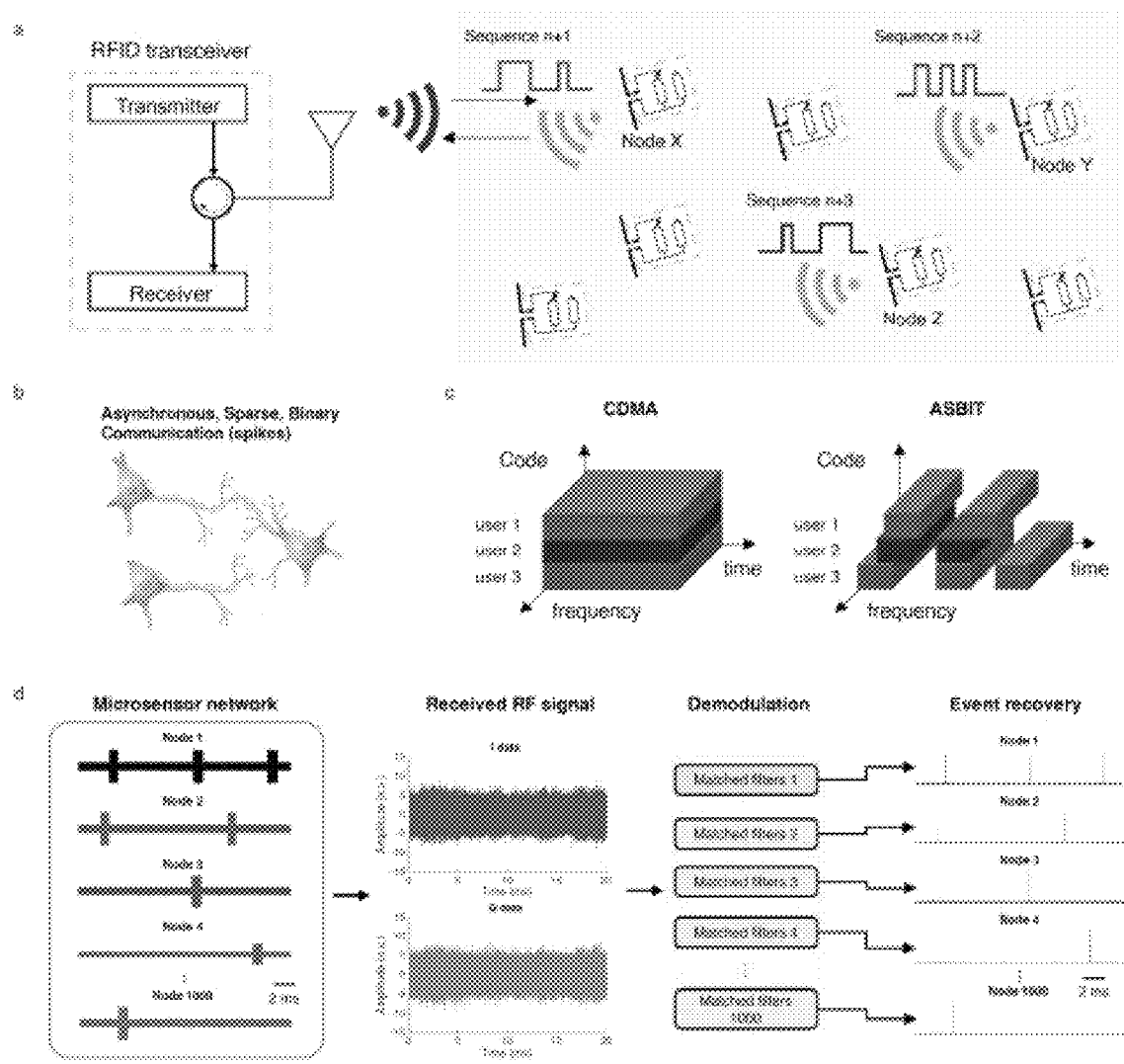
FIG. 8 illustrate block diagrams.

The ASBIT RF networking approach is shown in FIG. 8 for wireless transmission by ensembles of passive wireless sensors (Nodes X, Y, Z' as shown in "a" of FIG. 8). Each sensor transmits data packaged with a unique on-chip encoded RF identifier and, crucially, backscatters only when reporting an 'action potential' type event. The ASBIT idea is inspired by synaptic communication by ensembles of neurons firing action potentials in a brain network ("b" in FIG. 8) in being parallel, asynchronous, binary, yet sparse. Much unlike conventional code-division multiple access (CDMA), however, the neuron-inspired ASBIT scheme does not transmit any non-events, i.e., "zeros". Only meaningful information ("ones") above an event threshold is transmitted. As a consequence, good use can be made of key network resources, whether in an RF, optical or other communication medium in terms of the spectrum, code, and timing ("c" in FIG. 8). We show below how a single ASBIT link is scalable up to tens of thousands of user nodes where the sparsity of the target environment determines a fundamental limit for the system. A summary of the serial steps to unpack aggregate signals in the process of RF demodulation is shown the example "d" of FIG. 8, here for 1,000 autonomous nodes. The raw quadrature modulated (I/Q) data at the receiver (second panel from left) shows an aggregate simulated superposed signal. Given that data is encoded at each sensor with a unique identifier, the binary events across the ensemble can unpacked by a demodulation technique, here using matched filters (MF).

Figure 9:
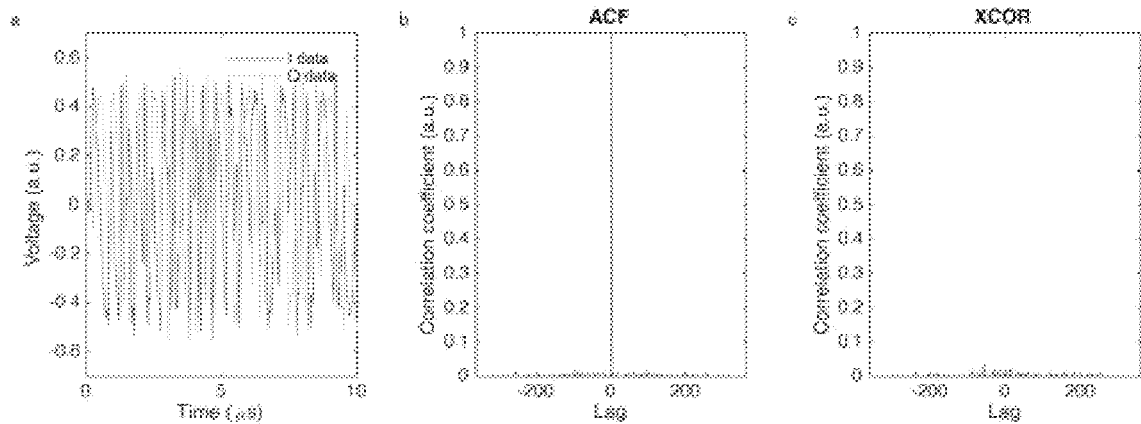
FIG. 9 are graphs.

The Gold Code is one of many choices was quasi-orthogonal cdes as the vehicle for the large-scale asynchronous sensor networks which can be employed in this invention. As an introductory example specifically of the Gold code, FIG. 9 shows the simulated I/Q waveform of data received from one RF sensor ("a" in FIG. 9) and the computed auto-correlation trace for its specific Gold code waveform while allowing for intrinsic residual clock offset ("b" in FIG. 9). "c" in FIG. 8 shows cross-correlation traces between this particular waveform and that of another Gold coded waveform, illustrating the basis for distinguishing events from multiple sensors while being largely immune from interference from other nodes in the network.

Figure 10:
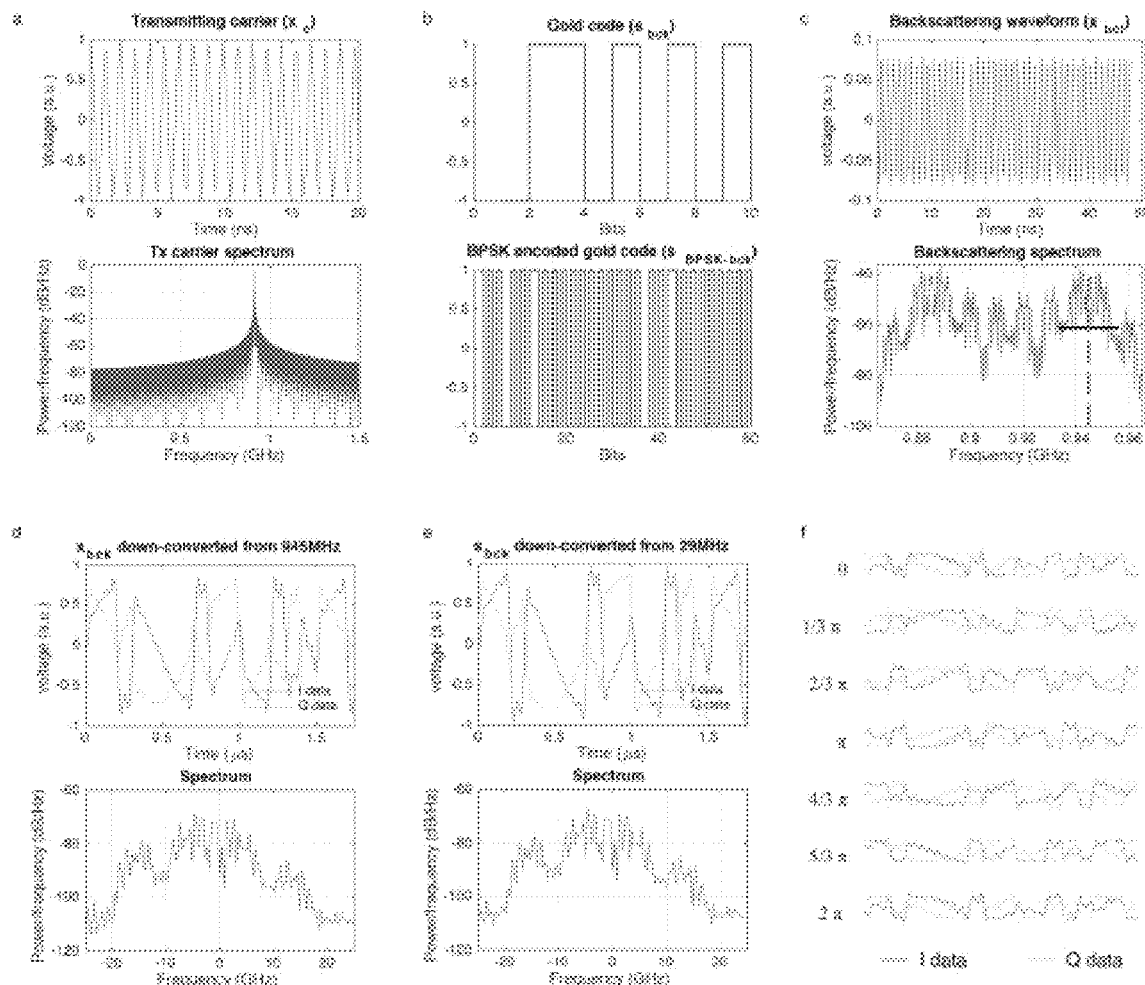
FIG. 10 are graphs.
Figure 11:
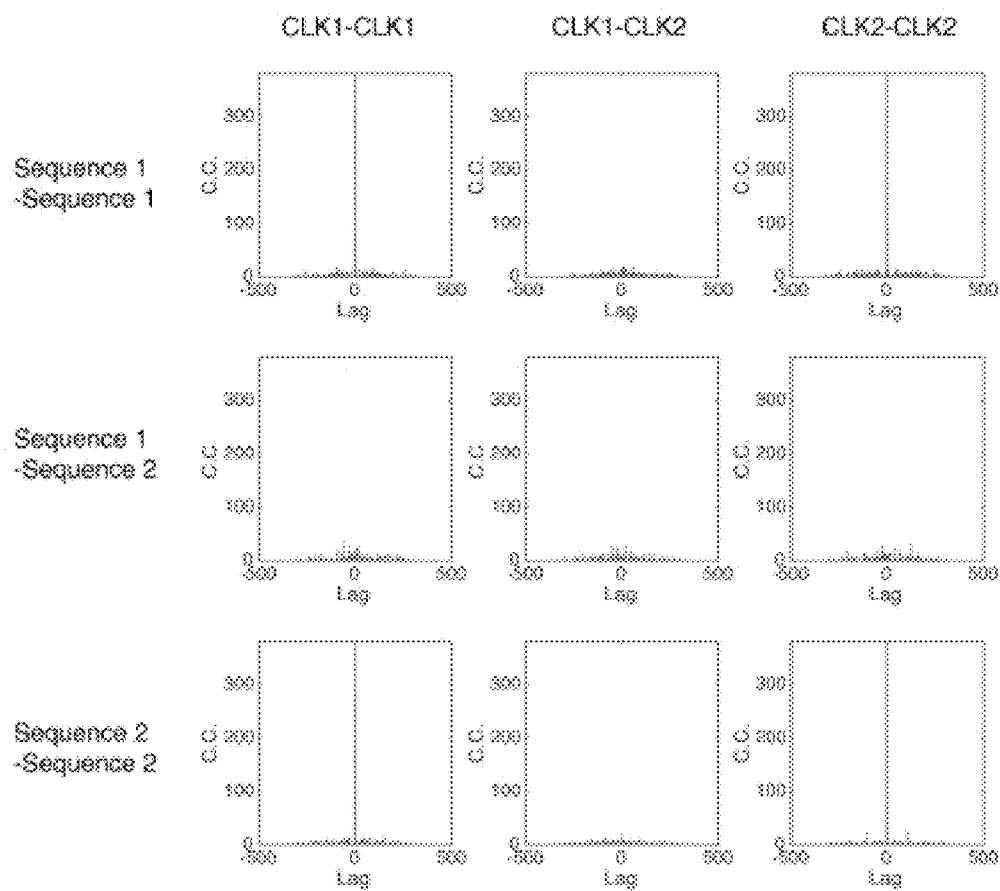
FIG. 11 are graphs.

In a simulation testbed designed to quantify the performance of an ASBIT network, we first synthesized all the relevant I/Q waveforms for a large number of sensors. We allowed for realistic operating conditions by including relevant features of a particular microchip we fabricated recently as a candidate for implantable neural sensors. A description of the synthesis is given in FIG. 10 and FIG. 11. The fabricated sub-mm size microchips consists of rectifier circuits to inductively harvest wireless RF energy, a free-running oscillator for the clock in a digital finite state machine (FSM), and a toggle-type modulator to generate the backscattered signal (overview in FIG. 12). For microscale sensors, especially those for biomedical implant purposes, housing an onboard high precision crystal oscillator or sophisticated clock stabilization circuitry is generally impractical due to size and power constraints. In case of the ultralow power, small footprint free-running oscillator in our ASICs, we had to account for clock frequency variance and drift in the simulations. The variance is caused by variations in chip power due to the near-far problem in energy harvesting (i.e. distance dependence of the transmitter (Tx) to a given sensor); the drift is caused by fluctuations in chip voltage supply due to circuit instabilities and fluctuations in ambient temperature. In particular since the unregulated on-chip voltage supply (VDD) is linearly dependent on captured RF energy, variations in VDD shift the clock frequency: a sensor closer to the RF hub benefits from a higher VDD resulting in higher amplitude and higher clock frequency of the backscattered signal.

Figure 13:
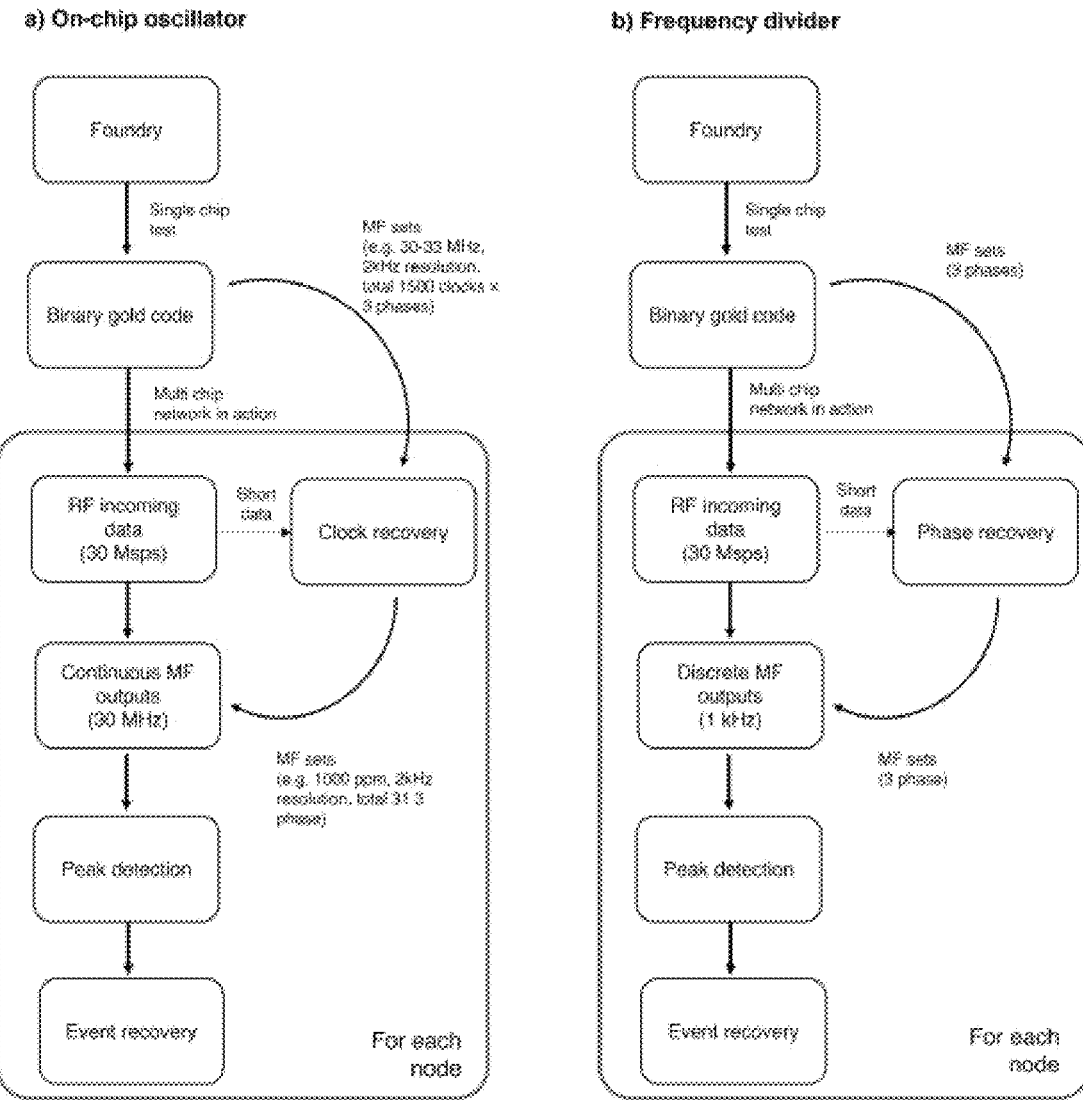
FIG. 13 illustrate flow diagrams.

The simulation testbed allowed us to systemically analyze key aspects of the proposed ASBIT protocol for a network on the scale of thousands of microchip sensors. The details of the computational pipeline for ensemble RF demodulation are illustrated in FIG. 13 in the case of a free-running oscillator as summarized below. To quantify the accuracy of data transmission, we define here an Event Error Rate (EER) as the number of errors per second while assuming a maximum event rate of 1 kHz. A missing event or any instance of false detection was counted as an event error. A number of factors impacting the EER were examined insofar as the accuracy of event detection via the demodulation process. We assumed somewhat arbitrarily a nominal duration of each event (bin size) is 1 msec.

Figure 12:
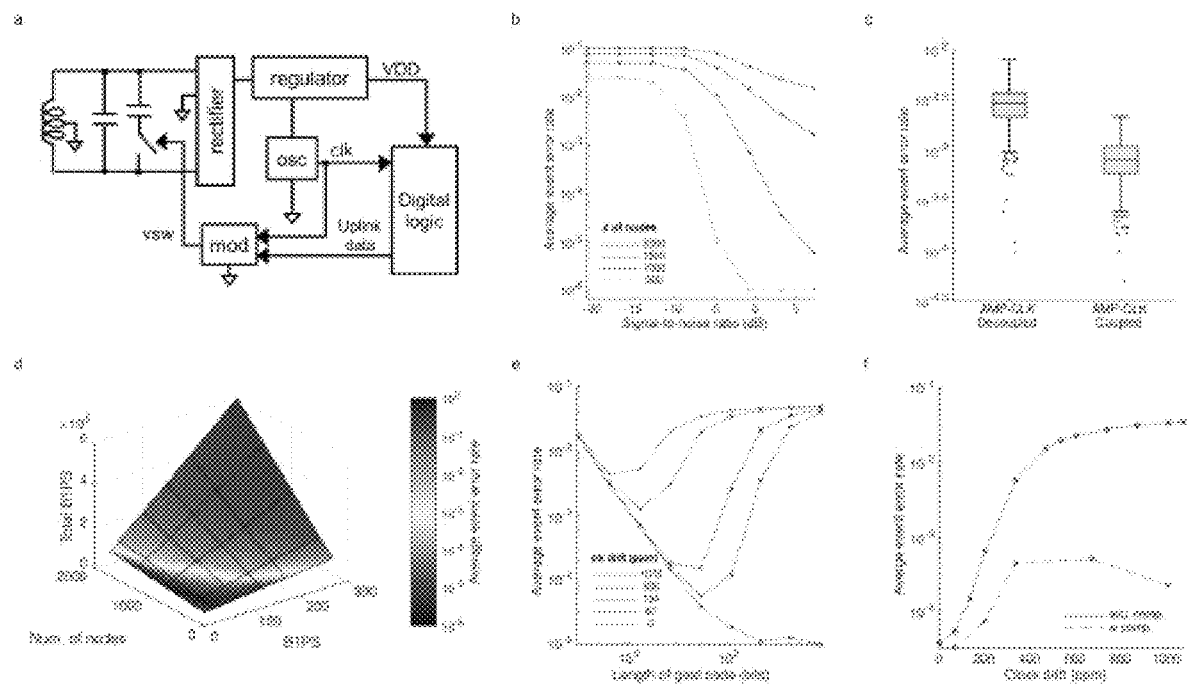
FIG. 12 illustrate a block diagram and graphs.
Figure 14:
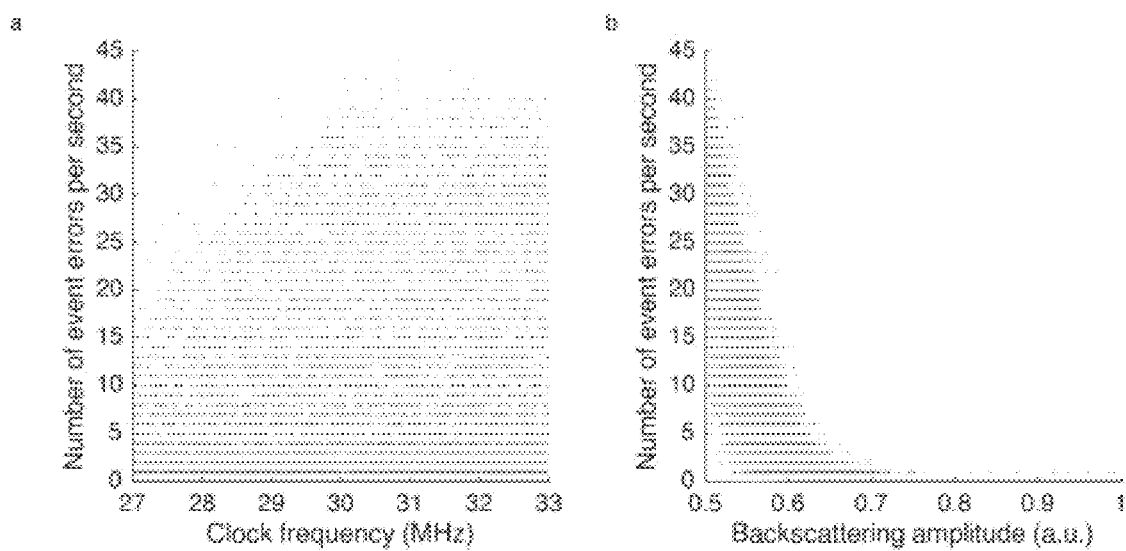
FIG. 14 are graphs.
Figure 15:
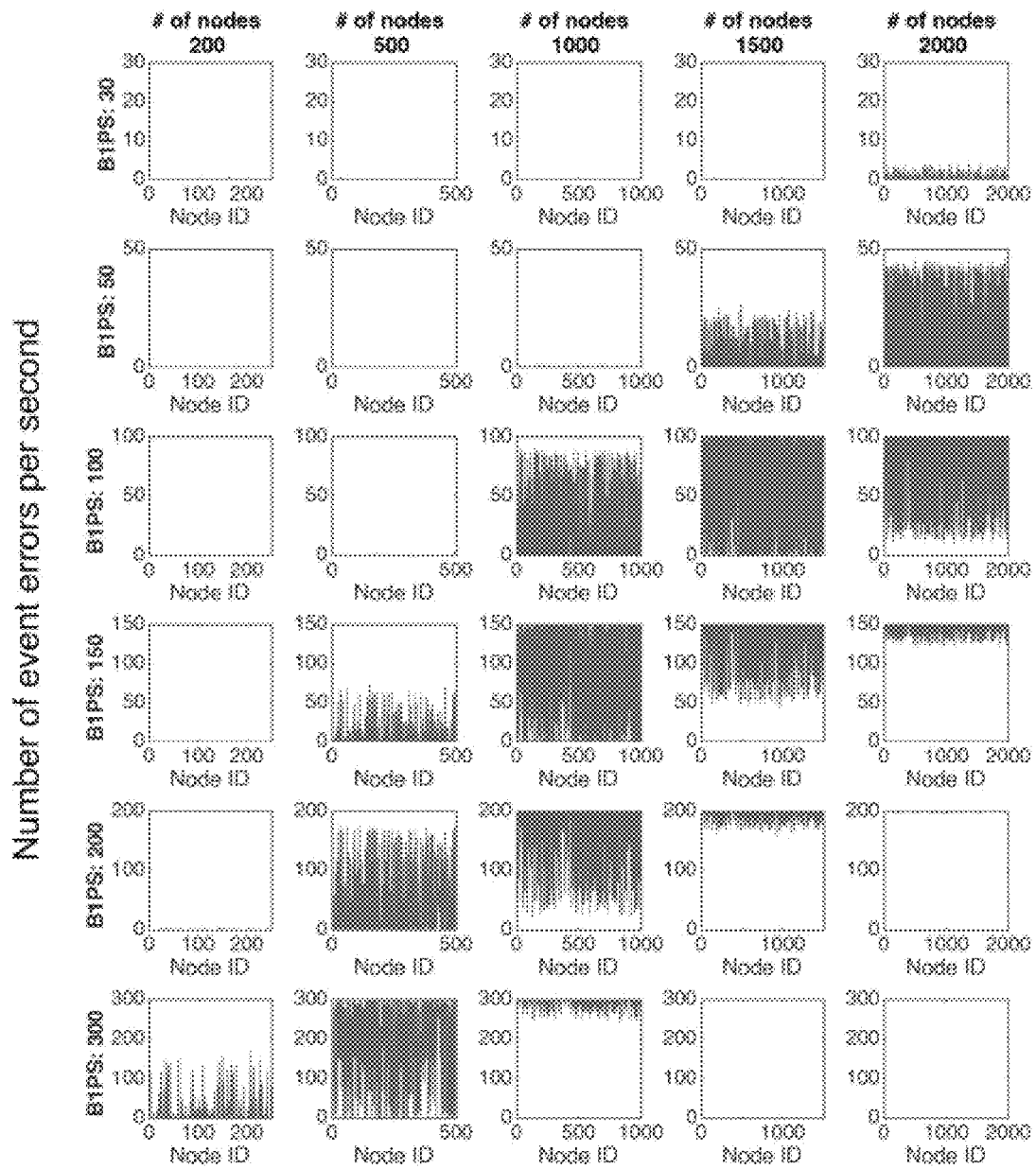
FIG. 15 are graphs.

We quantified how varying the overall network size impacts the fidelity of communication as a function of noise, i.e. the EER vs. the signal-to-noise ratio (SNR). As an example, "b" in FIG. 12 shows how a reasonably low EER of 10-3 can be achieved with one thousand nodes in the network. We note that while not near telecom values, an EER on the order of 10-3 is considered acceptable for a forward model-based application such as BMI-based neural prostheses. In the simulation, each node was assumed to be sparse, transmitting its signal at a 5% duty cycle, i.e. a statistical average event rate of 50 Hz with an event transmission duration of 1 msec (bin). "c" in FIG. 12 gives a statistical summary in terms of the quartile plots for a range of EER values across a population of 1,000 sensor nodes. The plot shows how most nodes lie near the median while a few outliers show a much lower EER. Next, we compared the situation between the case when the level of harvested RF power is coupled to the clock (frequency) vs. the case where the two are uncoupled. When the two are coupled (dependent variables), a lower EER is obtained for the ASBIT network compared to the uncoupled case (independent variables). Details of the analysis of the EER across the nodes are shown in FIG. 14 as a function of the clock frequency (in MHz) and the backscattered amplitude for the case when the harvested power and the clock are independent. As a multidimensional summary, FIG. 12 and FIG. 15 show how the aggregate sensor population event rate relates to the network capacity for the number of nodes ranging from 250 to 2,000; the plot was generated by multiplying the statistical event ('firing') rate by the number of nodes in evaluating the EER for the total network. As expected, the EER increases both with increasing firing rate and the number of nodes. Overall, it is the aggregate event sum that mainly determines the network communication performance. This result suggests that the ASBIT protocol can be flexible with a simple scaling rule: A smaller number of sensors allows for high event activity rates while a greater number constrains the network to sparser event rates.

At the same time, clock frequency drift and fluctuations add not insignificant computational complexity to demodulation and decoding in the ASBIT protocol. For the types of free-running on-chip oscillators used in our recent work, clock drifts can range anywhere from a few ppm to parts in a thousand in a given time interval. In that sense the above simulations summarized in FIG. 12 are idealized since clock drifts can affect the accuracy of communication. We evaluated the impact of on-chip clock drift on the same simulation testbench. FIG. 12 summarizes the computed EER over a range of average clock drift (in units of ppm, the nominal clock frequency of 30 MHz), under the assumption that the clock frequency can change randomly between individual transmission events from zero up to about ±1,005 ppm. The graph shows the penalty imposed by clock instability on the EER as a function of the bit length of the Gold code. For example, when the clock drift is below 134 ppm, using a Gold code of 512-bit length results in an EER lower than 10-3.5. Generally, as a design guide, a longer Gold code shows higher susceptibility to clock drift. Clock drift can be compensated at least up to a point by resorting to multiple MFs to account for the corresponding variances in the backscattered waveforms as shown in FIG. 12. Here, by using 31 sets of MFs (@2 kHz resolution), we could achieve 10-3.75 EER even with a clock drift of 1,005 ppm. However, the penalty incurred in using a large number of MFs is an increase in the computational burden in signal processing which can contribute to an increase in the overall system latency.

We designed a prototype wireless sensor ASIC to validate in in silico the simulation predictions of the ASBIT communication method. The design of the ultra-low-power, sub-mm sized, system-on-chip silicon die incorporated main pieces in FIG. 12, namely a low-voltage rectifier, a Gold code generator, a digital finite state machine, plus a BPSK-based modulator for backscattering. The 'communication' chips were fabricated in TSMC's 65 nm mixed-signal/RF low-power CMOS process.

Figure 16:
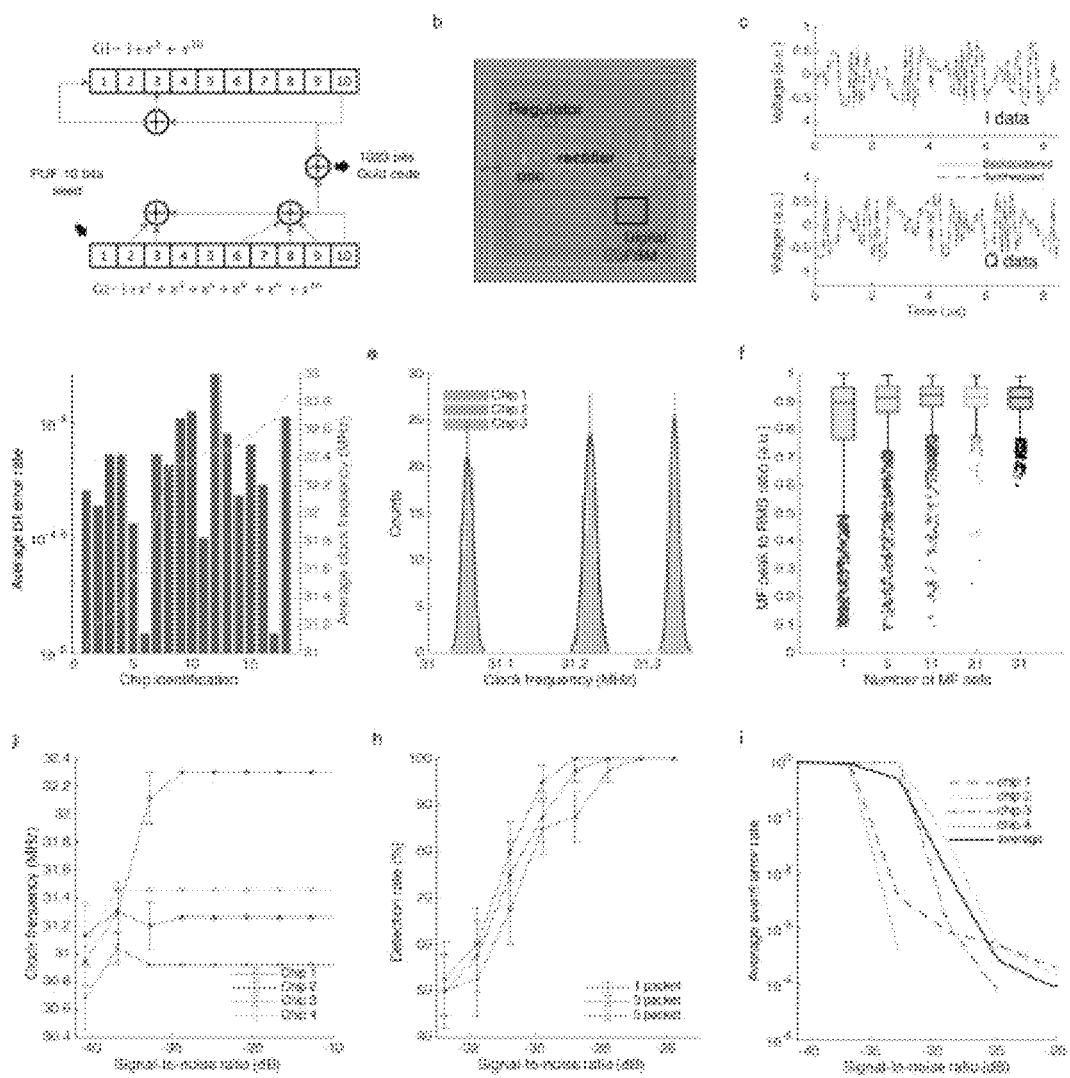
FIG. 16 are graphs.
Figure 17:
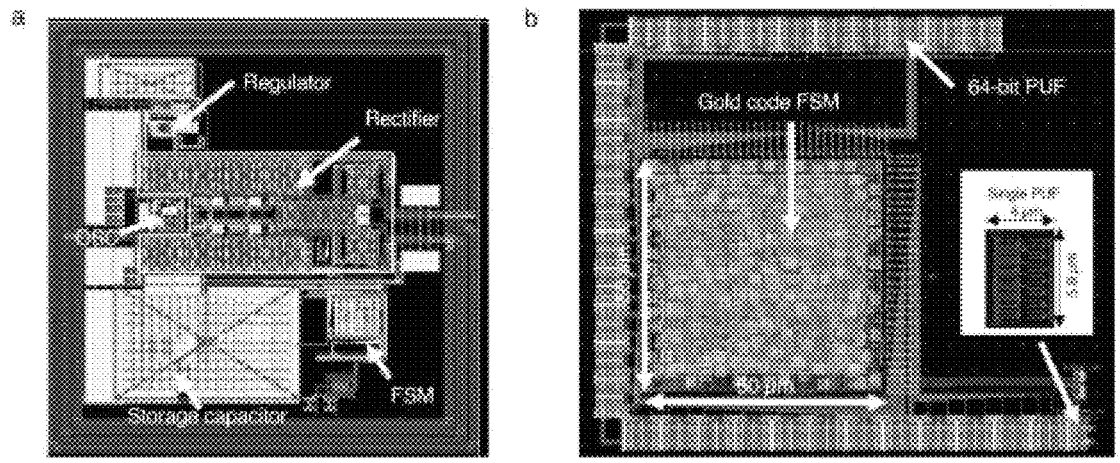
FIG. 17 are diagrams.
Figure 18:
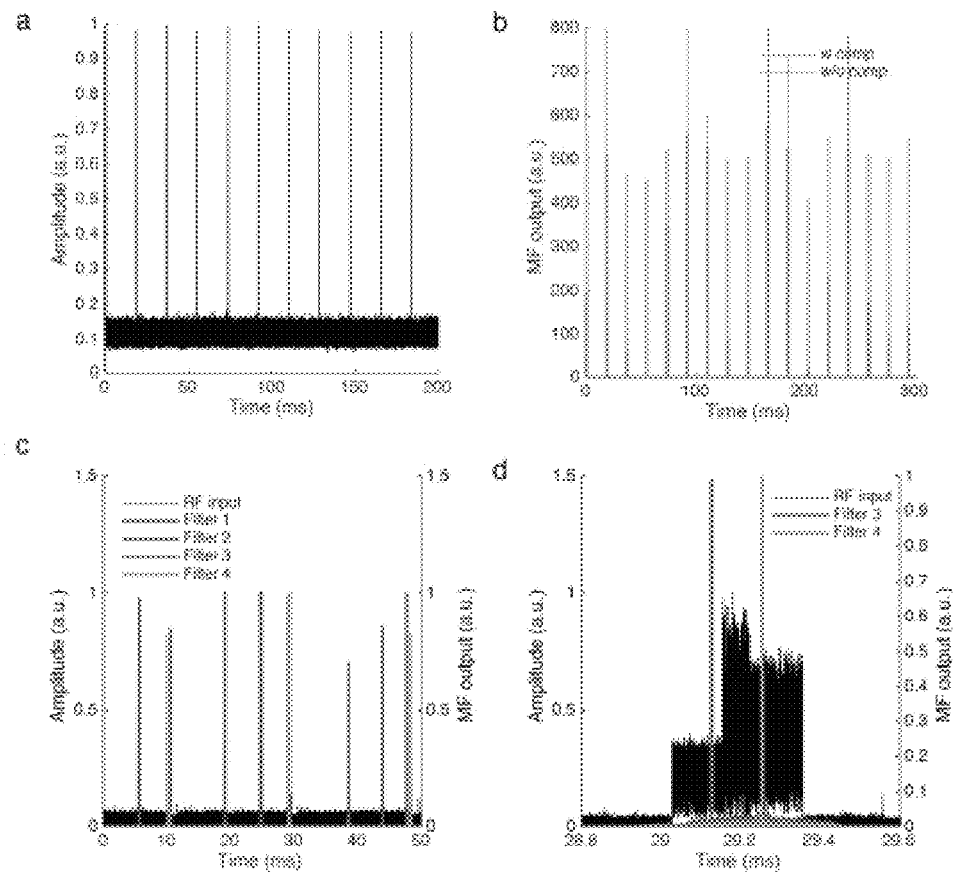
FIG. 18 are graphs.

The diagram of FIG. 13 shows the implementation of our Gold code generator, here for 1023 bits, using preferred pairs of m-sequences and linear feedback shift resistors (LFSR). To generate a unique quasi-orthogonal sequence for each sensor without resorting to chip post-processing, we configured a physical unclonable function (PUF) to seed the Gold code generator. Each sensor chip uses its own 10-bit PUF to synthesize a 1023-bit unique Gold code. An advantage of using this approach is that the very small footprint compared to e.g. a pseudo-random number generator (see FIG. 17 for the actual ASIC layout). FIG. 16 shows the footprint of the fabricated prototype 600 µm×600 µm CMOS chip. Most of the chip area is reserved for a capacitor bank to stabilize the voltage supply; the digital finite-state machine (FSM) only requires an area of some 50 µm×50 µm. The circuit parameters in this particular ASIC were set to generate Gold code backscattered transmission every 20 µsec as shown in FIG. 18 so as to compare experimental results with the simulations. FIG. 16 shows a piece of measured I/Q data (on µsec timescale of a Gold code packet) from the wireless chip in comparison with output from the synthesizer tool we developed, to demonstrate that the tool used in the RF simulation is capable of regenerating the I/Q data from the chips at high fidelity.

We then characterized the bit error rate (BER) for the fabricated chips, each encoding a total 2047-bit Gold code, PUF-seeded sequence. We tested the consistency of the chips in generating the exact same Gold code pattern over a finite length of time. For a meaningful statistical test we measured a total of 18 post-processed wireless chips, the data summarized in the histogram of FIG. 16. Most of the chips achieved BER below 10-4 in a demonstration of Gold code performance at a sufficient level of accuracy e.g. for BMI use. The plot of FIG. 16 also indicates the spread of clock frequencies across this ensemble of 18 chips, frequency ranging from 31 MHz to 33 MHz and being dependent on the incoming RF level. We also characterized in further statistical detail the clock drift over time for three randomly chosen chips and found this to be around ±1,000 ppm (FIG. 16). Due to the finite drift, the waveform of the Gold code packet for any given chip varied across individual transmission events whereby the correlation values obtained using one matched filter became inaccurate. However, the use of multiple sets of MFs to compensate for clock drift led to a comparable correlation output for all packet transmission events as demonstrated in FIG. 18. The statistical plot of FIG. 16 shows the peak MF output during the packet transmission compared to its RMS level during a non-transmission period, normalized for each chip, and the dependence on the number of matched filters. Note how using only a single MF yield a value range from 0.1 to 1 so that some recovered events yielded only 10% of the maximum possible correlation value. By contrast, when the demodulation deployed a set of 31 MFs, outliers were captured as well (gray colored plot in FIG. 16) whereby 75% of events achieved 85% value relative to the maximum correlation value.

Figure 19:
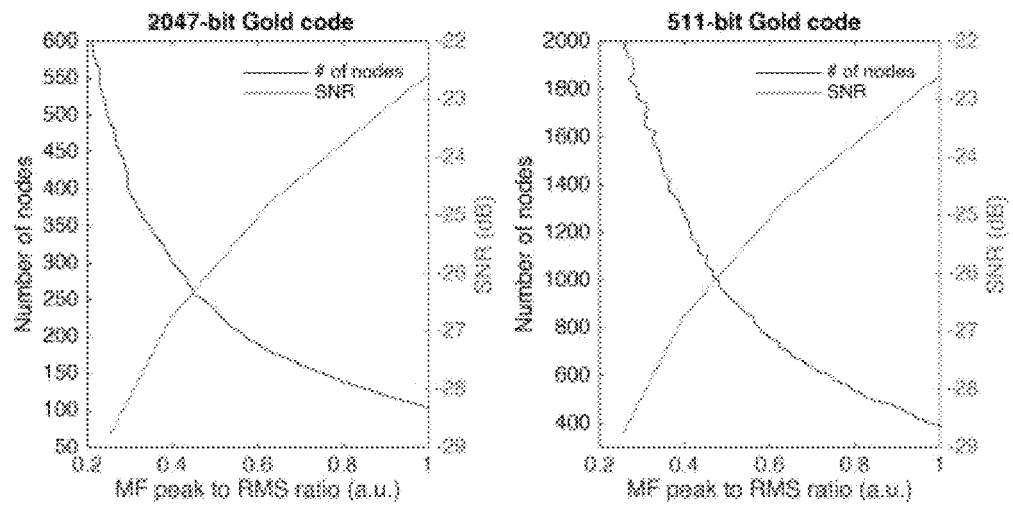
FIG. 19 are graphs.
Figure 20:
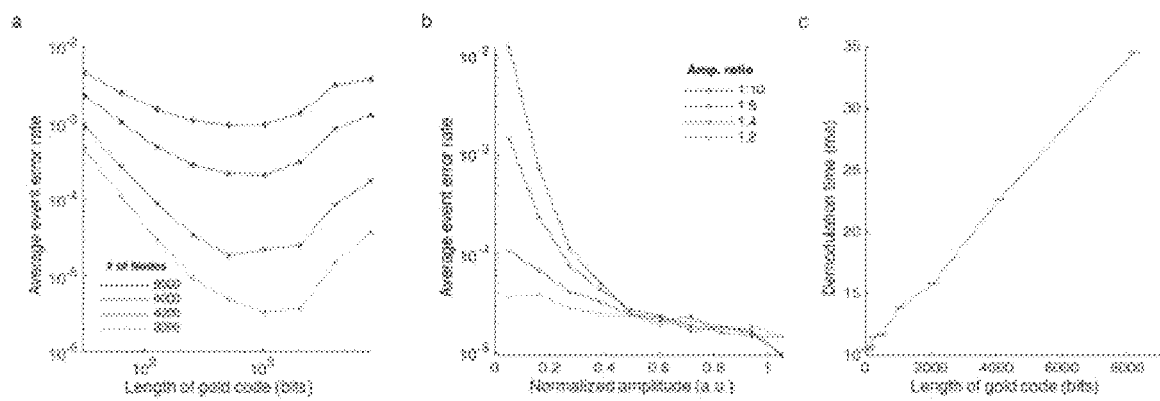
FIG. 20 are graphs.

From the population of post-processed 18 chips, we chose four chips for further experiments (each reliably transmitting a non-overlapping Gold code signal every 20 milliseconds). FIG. 18 (for 4 MFs) shows the amplitude of the received transient RF signal and the correlation output from MF sets specifically designed for each chip. One sees how this method differentiates a target packet even when two packets have undergone an interfering collision. We added a proxy noise level to mimic the interference from a background ensemble of chips. FIG. 16 shows the recovery of clock frequency from four chips even in the presence of an SNR=−28.77 dB, an equivalent noise contribution by 480 chips in the wireless network, each with an SNR of 3.22 dB (FIG. 19). We also tested the ability to detect a packet sequence within a short time interval, here corresponding to transmission of 1 to 5 Gold code packets (FIG. 16). The experiment showed how one can achieve a 100% detection rate from four chips even with an SNR of −26.77 dB, equivalent to 300 chips active in the overall network. Last, we evaluated the variance in EER for the set of four chips as illustrated in FIG. 16 using 2047-bit or 511-bit Gold codes, respectively. We could achieve EER=10-3.55 for an SNR of −24.77 dB, equivalent to 180 or 720 other background nodes running in the network, respectively. In sum, the experiments support the results which show that, even with the penalties imposed by clock drift and fluctuations, the ASBIT protocol is scalable to hundreds of nodes and capable of operating in a relatively modest SNR environment, yet quite immune from collisions.

As an alternative to the on-chip reliance of free-running clocks, we investigated role of the RF baseband downlink as possible frequency reference for circumstance where this is potentially advantageous and technically practical. Using the baseband RF for timing has been demonstrated for passive RFID tags whereby an incoming RF frequency (here 900 MHz) is down-converted to generate a lower frequency clock. One particular choice is a multiple stage True Single Phase Clocked (TSPC) frequency divider shown schematically in FIG. 21 as embedded in our monolithic sensor. A divider approach offers the benefit of negligible clock variance and nearly independence from energy harvesting efficiency. Note that a frequency divider approach does not imply network synchrony since the phases of individual on-chip frequency references (clocks) will differ due to phase lag arising e.g. from random start-up in each chip's starting circuit. Here we show results of a simulation-based analysis in assessing the performance of the ASBIT networking protocol while assuming identical frequency divider circuits for all sensors.

Figure 21:
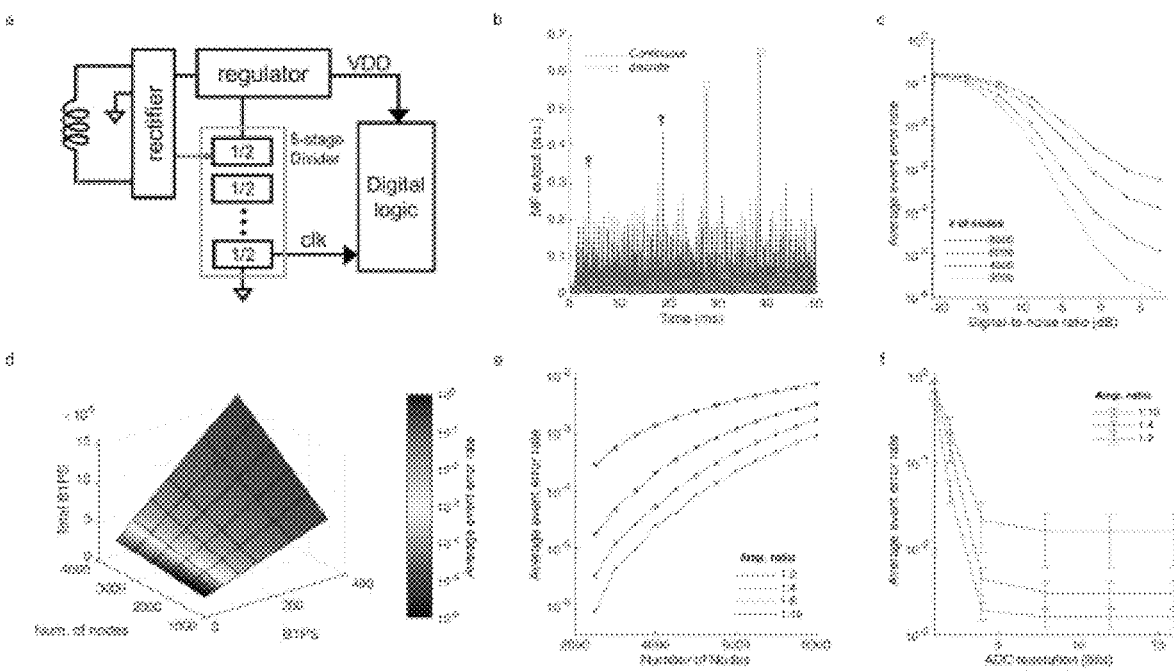
FIG. 21 are graphs.
Figure 22:
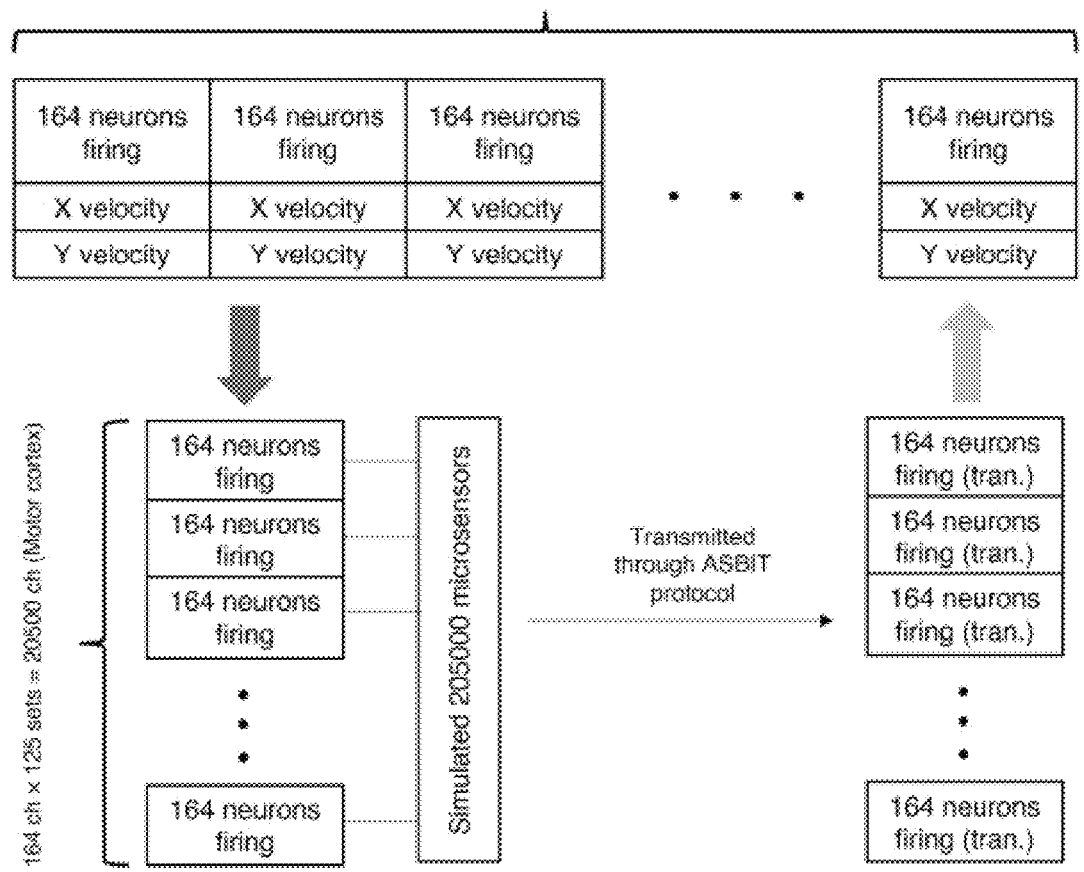
FIG. 22 are diagrams.
Figure 23:
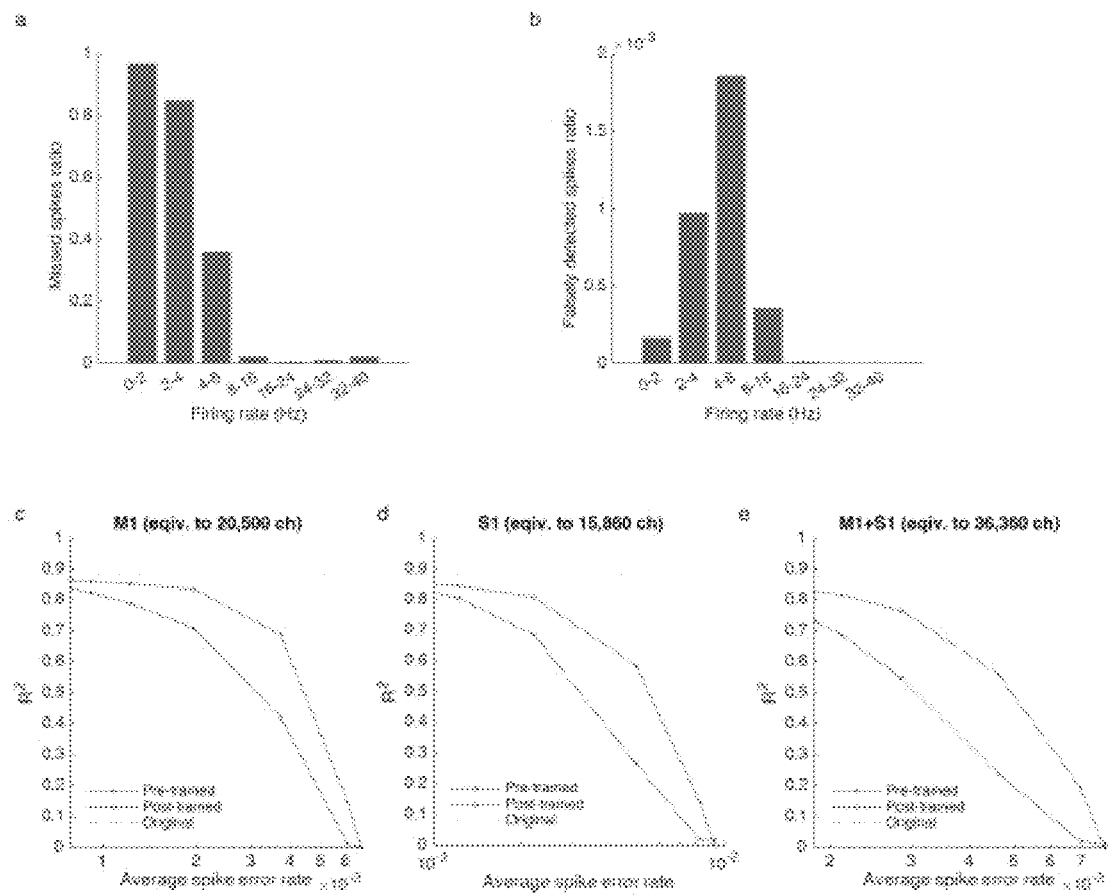
FIG. 23 are graphs.

Given an expected clock frequency for each sensor, we can estimate the timing sequences across the sensor ensemble as the backscattered signal are generated. In contrast to the case of sensors with on-chip oscillators, the ASBIT demodulation step can now be performed computationally rather simply. FIG. 21 shows how applying a single MF in a predefined time window allows the direct exclusion of false detection hence improving the EER. FIG. 21 in particular shows how, in the clock divider approach, our ASBIT protocol can readily accommodate a significantly larger number of nodes compared to the case of an on-chip oscillator. In this example an ensemble of 4,000 sensors can achieve an EER of 10-4.5 for an SNR is 3.33 dB assuming a 50 Hz average event detection rate for each node. Further, the total aggregate event (spike) rate across the network, i.e. the network capacity, can now be increased as illustrated in the composite FIG. 21. If we again were to assume that an EER on the order of 10-3 is acceptable for an application such as BMI-based neural prostheses, the simulations predict that the ASBIT protocol can communicate an aggregate of up to 4×105 spike events per second. The expected value of EER does depend on the length of the Gold code; FIG. 23 shows predictions which suggests an optimal range of around 1024 bits to 2048 bits depending on the size of the network.

We also re-examined the near-far problem, here for a network of inductively powered RF sensors. We first fixed the RF amplitude ratio between 'near' sensors and 'far' sensors as 2:1. The results are shown in FIG. 21 where e.g. an EER of 10-3.8 can be achieved in the network consisting of 4,000 nodes for a 6:1 near/far ratio in the backscattered signal amplitudes. FIG. 23 shows that the most of bit errors occur at the "far" sensors while "near" sensors are unaffected by the other nodes. A practical aspect in the near-far problem arises from limitations in hardware performance such as bit resolution and dynamic range and other details at the transceiver hub. We note that in most software-defined radios (SDR), an automatic gain control scales the incoming data for the ADC and thus determines the dynamic range based on the strongest signal from the 'near' sensors. In FIG. 21, we analyzed the performance of the ASBIT for a range of various ADC resolutions to show how an 8-bit ADC can achieve an EER comparable to in a 16-bit ADC. The outcome may be due to effective bit protection by the Gold code sequence which spreads out the signal in time domain while also assuming that linear superposition holds for signals from multiple nodes.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A method comprising:
providing an ensemble of up to ten thousand distributed sensors;
delivering radio frequency (RF) power to each sensor by inductive near-field coupling by a magnetic field projected by an epidermal transmit (Tx) coil;
in each individual sensor, detecting a sparse binary event in its immediate environment;
reporting the detected sparse binary event to an external RF receiver hub asynchronously and with low latency; and
minimizing error rates due to statistical data packet collisions in asynchronous telemetry by assigning to each sensor a unique address according to a particular address scheme where each address is one function from an infinite set of mathematically orthogonal functions convolved with a physically unclonable function, enabling a simultaneous detection from up to ten thousand points without interference at a common receiver.

2. The method of claim 1 wherein each of the sensors has an application-specific integrated circuit (ASIC) implemented as a system-of-chip in monolithic silicon that combine sensor circuits with RF telemetry circuits on one integrated microscale platform.

3. The method of claim 2 wherein the ASIC is designed for binary phase shift key (BPSK) or other types of digital signal modulation which accommodates encoding of the set of orthogonal address functions.

4. The method of claim 1 wherein the ensemble of distributed sensors is implanted in a body or on a body.

5. The method of claim 1 wherein the ensemble of distributed sensors is applied to a surface of a skin or below the skin as a distributed implant.

6. A system comprising:
a plurality of independent sensors, each of the independent sensors assigned a unique address according to a particular address scheme where each address is one function from an infinite set of mathematically orthogonal functions convolved with a physically unclonable function;
an epidermal transmit (Tx) coil, the Tx coil delivering radio frequency (RF) power to each of the plurality of independent sensors, the Tx coil capturing asynchronous data emitted from each of the plurality of sensors by radio frequency (RF) backscattering; and an external radio frequency (RF) receiver hub.

7. The system of claim 6 wherein each of the independent sensors is an application-specific integrated circuit (ASIC).

8. The system of claim 7 wherein the ASIC is designed for binary phase shift key (BPSK) modulation.

9. The system of claim 6 wherein the plurality of independent sensors is implanted in a body or on the body.

10. The system of claim 6 wherein the plurality of independent sensors is applied to a surface of a skin.

11. A method comprising:
providing a communication protocol between an external RF transceiver hub and an ensemble of up to about ten thousand distributed individual sensors;
in each individual sensor, detecting a sparse binary event in its immediate environment;
reporting the detected sparse binary event to an external RF hub asynchronously and with low latency; and
minimizing error rates due to statistical data packet collisions in asynchronous telemetry by assigning each sensor a unique address according to a particular address scheme where each address is one function from an infinite set of mathematically random or orthogonal functions convolved with a physically unclonable function, enabling the simultaneous detection from up to ten thousand points without interference at the common receiver.

12. A system for biomedical diagnostics comprising:
an asynchronous wireless network of biomedical event sensors in contact with biological tissue, each sensor configured to receive power by inductive near-field coupling from a magnetic field projected by an epidermal transmit (Tx) coil and configured to detect a sparse aperiodic event in its immediate environment, and, upon detection, transmit data representing the sparse aperiodic event, each sensor assigned a unique network address comprising a mathematical function from a set of mathematically orthogonal functions.

13. The system of claim 12, further comprising:
an external transceiver configured to asynchronously receive the data from each of the sensors.

14. The system of claim 12, wherein the unique network address comprises a convolution of a physically unclonable function with a mathematically orthogonal function.

15. The system of claim 14, wherein the network comprises up to ten thousand sensors.

16. A method for biomedical diagnostics comprising the steps of:
detecting sparse aperiodic events with an asynchronous wireless network of up to ten thousand biomedical event sensors in contact with biological tissue, each sensor configured to receive power by inductive near-field coupling from a magnetic field projected by an epidermal transmit (Tx) coil and configured to detect a sparse aperiodic event in its immediate environment, wherein each sensor is assigned a unique network address comprising a mathematical function from a set of mathematically orthogonal functions; and
upon detection, transmitting data representing the sparse aperiodic event to a transceiver.

17. The method of claim 16, wherein each unique address comprises a convolution of a physically unclonable function with a mathematically orthogonal function.

\* \* \* \* \*